United States Patent
Aschmann et al.

(10) Patent No.: US 9,095,383 B2
(45) Date of Patent: Aug. 4, 2015

(54) BONE-DERIVED SPACER ASSEMBLY

(75) Inventors: Felix Aschmann, Basel (CH); Justin Coppes, Downingtown, PA (US); Robert J. Delurio, Aston, PA (US); Benjamin S. Barrall, Conshohocken, PA (US); David Chow, West Chester, PA (US); Nicholas Angert, Paoli, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 260 days.

(21) Appl. No.: 13/061,155

(22) PCT Filed: Aug. 28, 2009

(86) PCT No.: PCT/US2009/055428
§ 371 (c)(1),
(2), (4) Date: Feb. 28, 2011

(87) PCT Pub. No.: WO2010/025408
PCT Pub. Date: Mar. 4, 2010

(65) Prior Publication Data
US 2011/0160773 A1    Jun. 30, 2011

Related U.S. Application Data

(60) Provisional application No. 61/092,655, filed on Aug. 28, 2008.

(51) Int. Cl.
*A61B 17/70* (2006.01)
(52) U.S. Cl.
CPC .................................. *A61B 17/7065* (2013.01)

(58) Field of Classification Search
USPC ..................... 606/246–249; 623/17.11–17.16
See application file for complete search history.

(56) References Cited

U.S. PATENT DOCUMENTS

| | | | |
|---|---|---|---|
| 6,102,950 A * | 8/2000 | Vaccaro | 623/17.16 |
| 6,899,716 B2 * | 5/2005 | Cragg | 606/86 R |

(Continued)

FOREIGN PATENT DOCUMENTS

| | | |
|---|---|---|
| CN | 101053537 | 10/2007 |
| WO | 2006/064356 | 6/2006 |

(Continued)

OTHER PUBLICATIONS

International Preliminary Report on Patentability and Written Opinion, dated Mar. 1, 2011, received from the European Patent Office in connection with International Application No. PCT/US2009/055428.

*Primary Examiner* — Jan Christopher Merene
*Assistant Examiner* — Steven Cotroneo
(74) *Attorney, Agent, or Firm* — Meunier Carlin & Curfman LLC

(57) ABSTRACT

An allograft interspinous spacer for implantation into an interspinous space located between spinous process of adjacent vertebrae. The spacer preferably includes a body, a core and a plurality of deployable retainers. The body may be operatively associated with the plurality of deployable retainers. In use, after the body has been inserted into the interspinous space, the plurality of retainers is deployed so that they prevent migration of the spacer. The core is preferably sized and configured to be inserted and/or moved into operatively engagement with the body to deploy the plurality of retainers.

25 Claims, 26 Drawing Sheets

(56) References Cited

U.S. PATENT DOCUMENTS

| | | | |
|---|---|---|---|
| 7,931,674 B2 * | 4/2011 | Zucherman et al. | 606/249 |
| 8,092,535 B2 * | 1/2012 | Zucherman et al. | 623/17.11 |
| 8,128,702 B2 * | 3/2012 | Zucherman et al. | 623/17.16 |
| 8,157,841 B2 * | 4/2012 | Malandain et al. | 606/249 |
| 2005/0245937 A1 * | 11/2005 | Winslow | 606/90 |
| 2006/0241614 A1 * | 10/2006 | Bruneau et al. | 606/69 |
| 2006/0264938 A1 * | 11/2006 | Zucherman et al. | 606/61 |
| 2006/0271049 A1 * | 11/2006 | Zucherman et al. | 606/61 |
| 2007/0032790 A1 | 2/2007 | Aschmann et al. | |
| 2008/0177312 A1 | 7/2008 | Perez-Cruet et al. | |
| 2009/0254185 A1 | 10/2009 | Dollinger | |

FOREIGN PATENT DOCUMENTS

| | | |
|---|---|---|
| WO | 2007075843 A2 | 7/2007 |
| WO | 2008013960 A2 | 1/2008 |
| WO | 2008/088613 | 7/2008 |

* cited by examiner

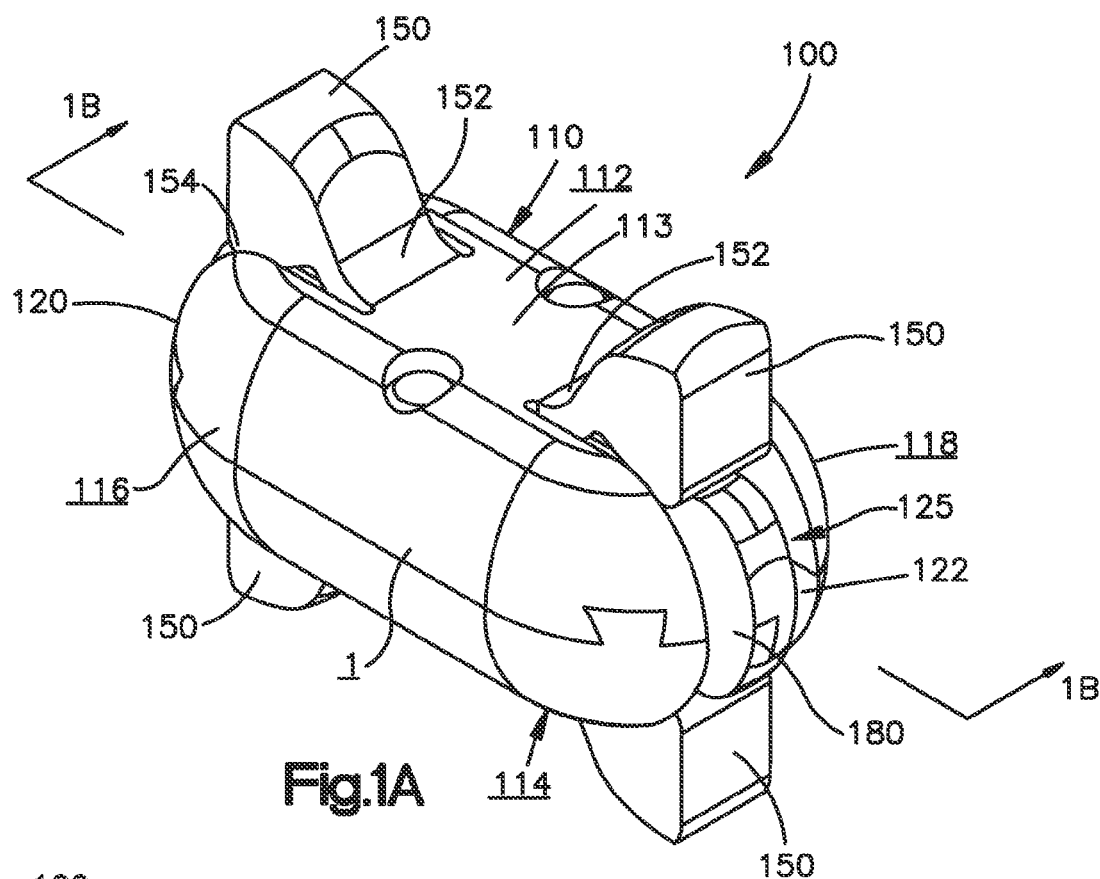
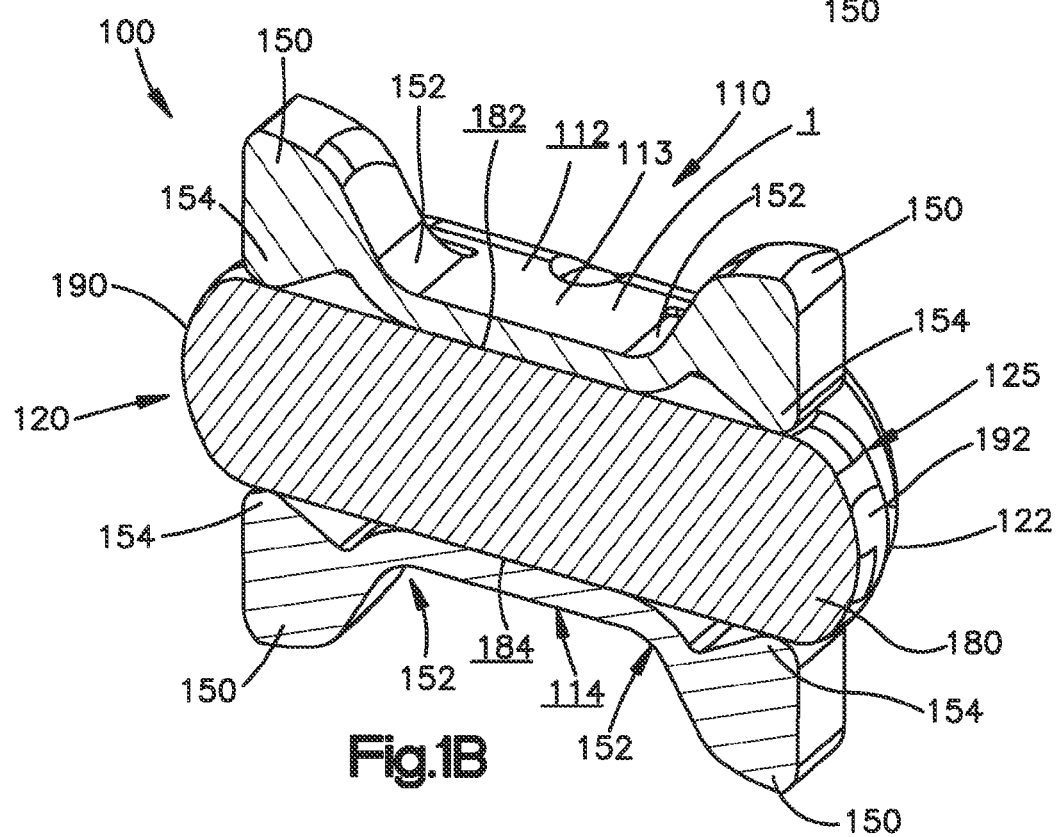

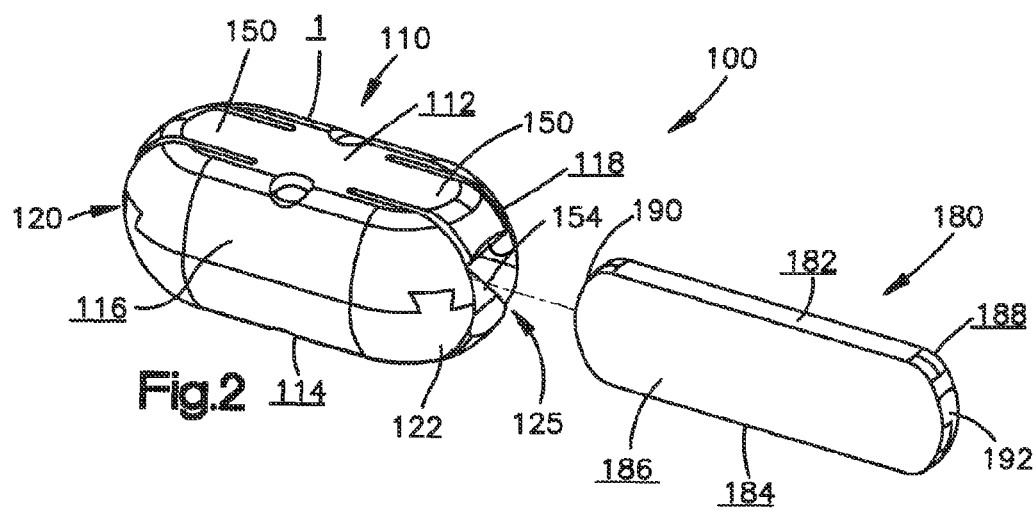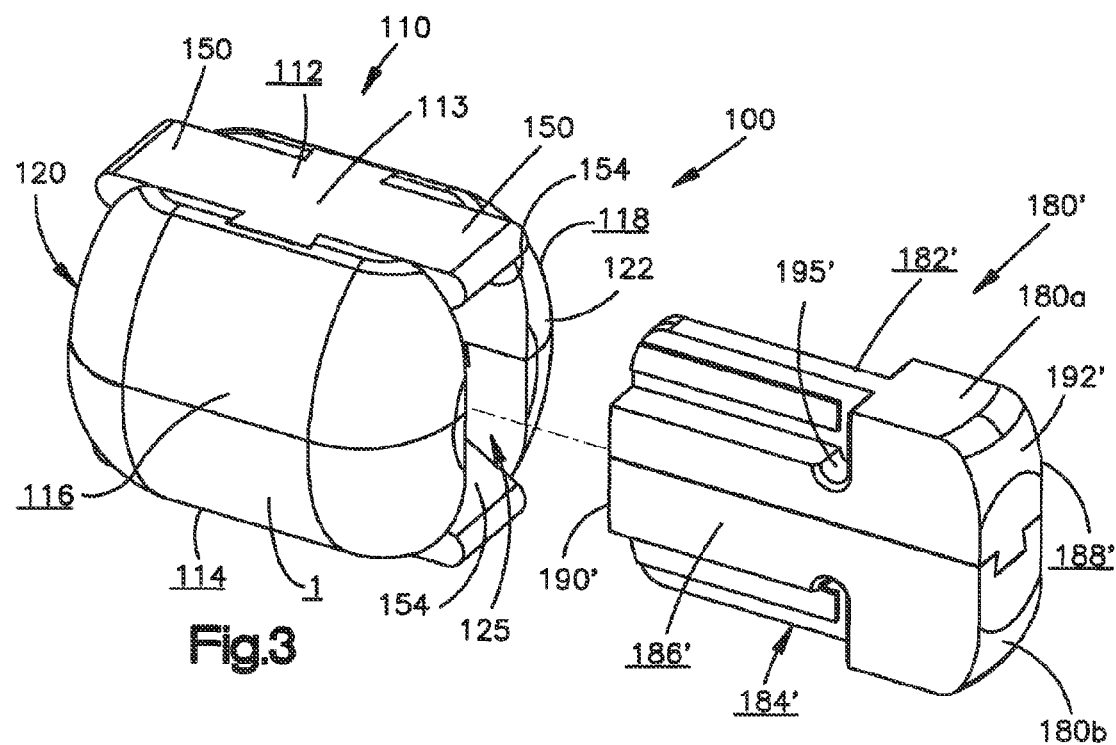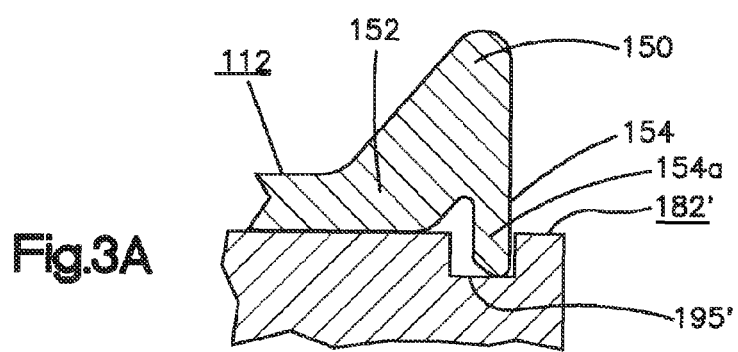

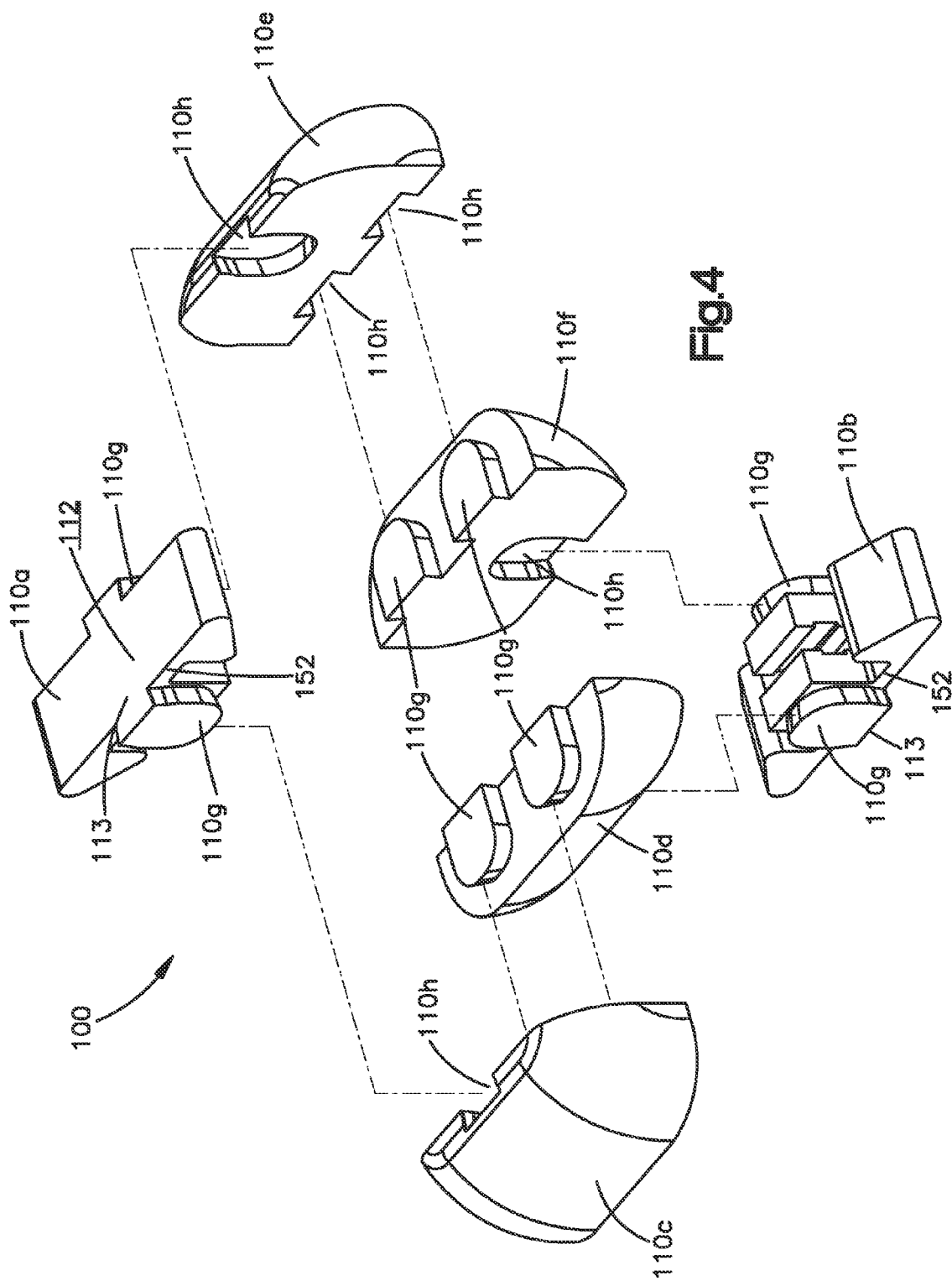

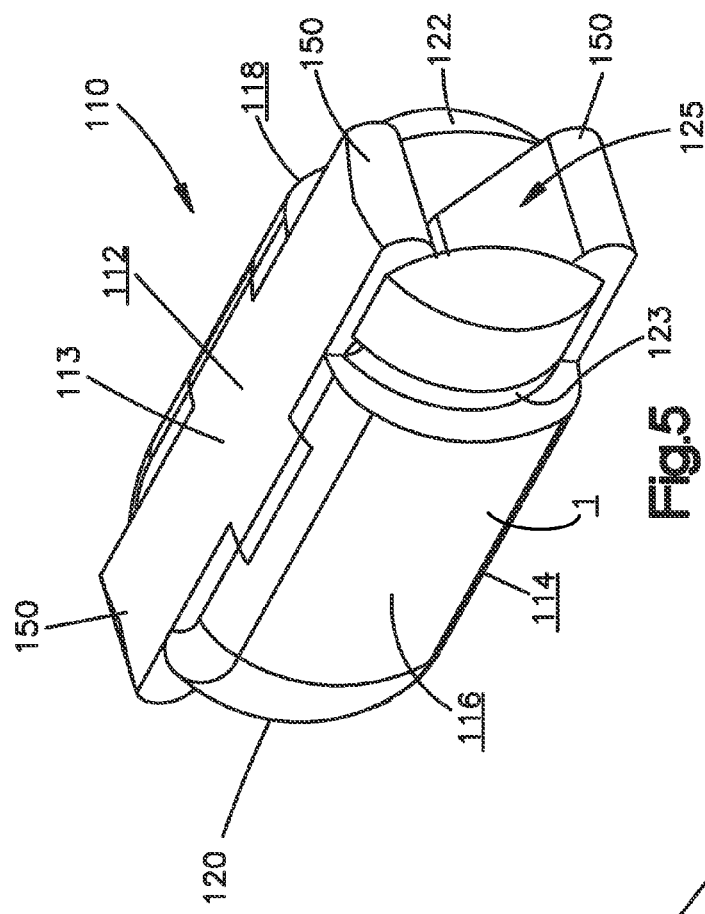
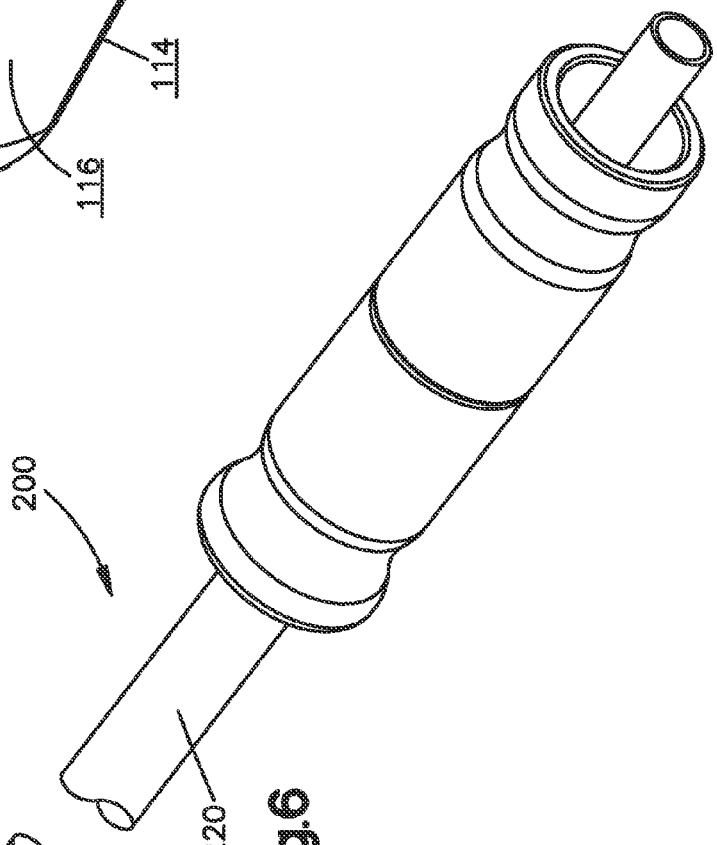
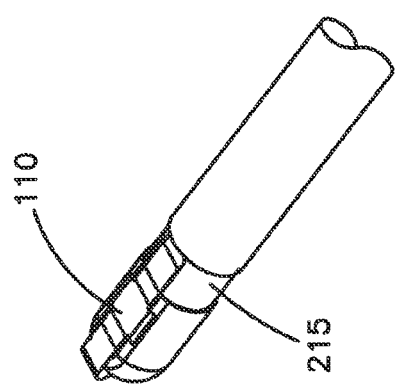

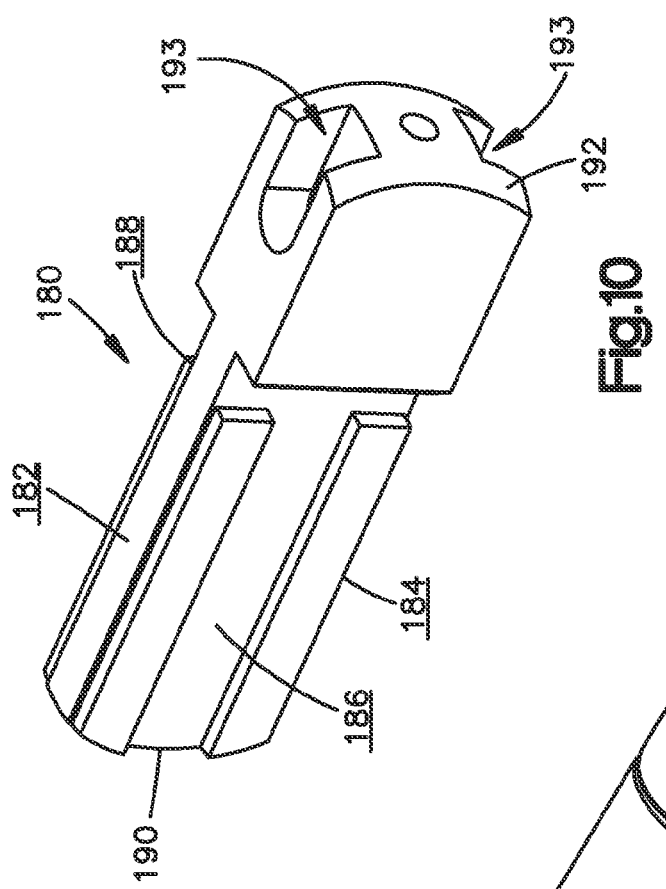
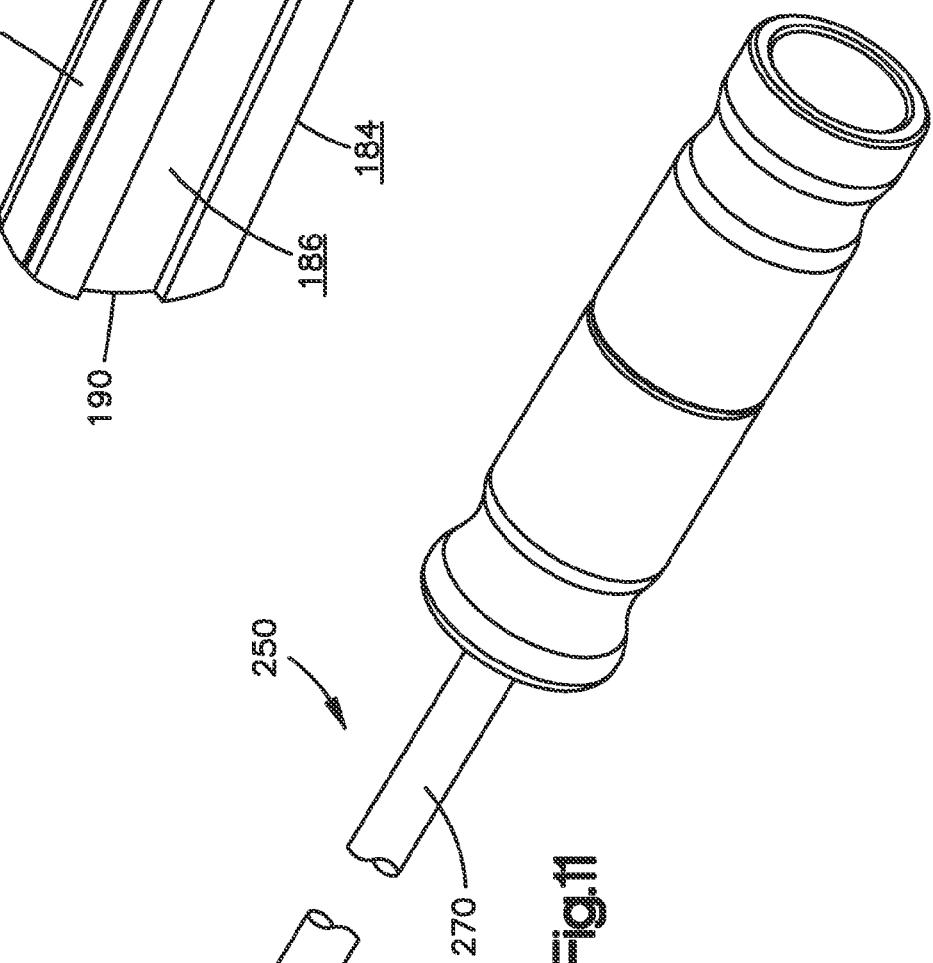
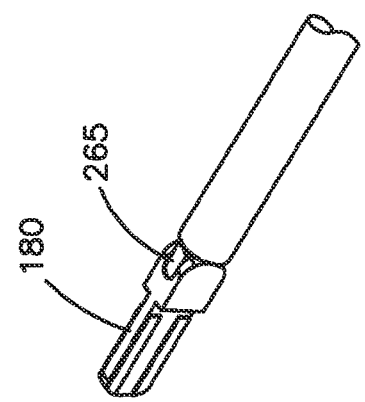

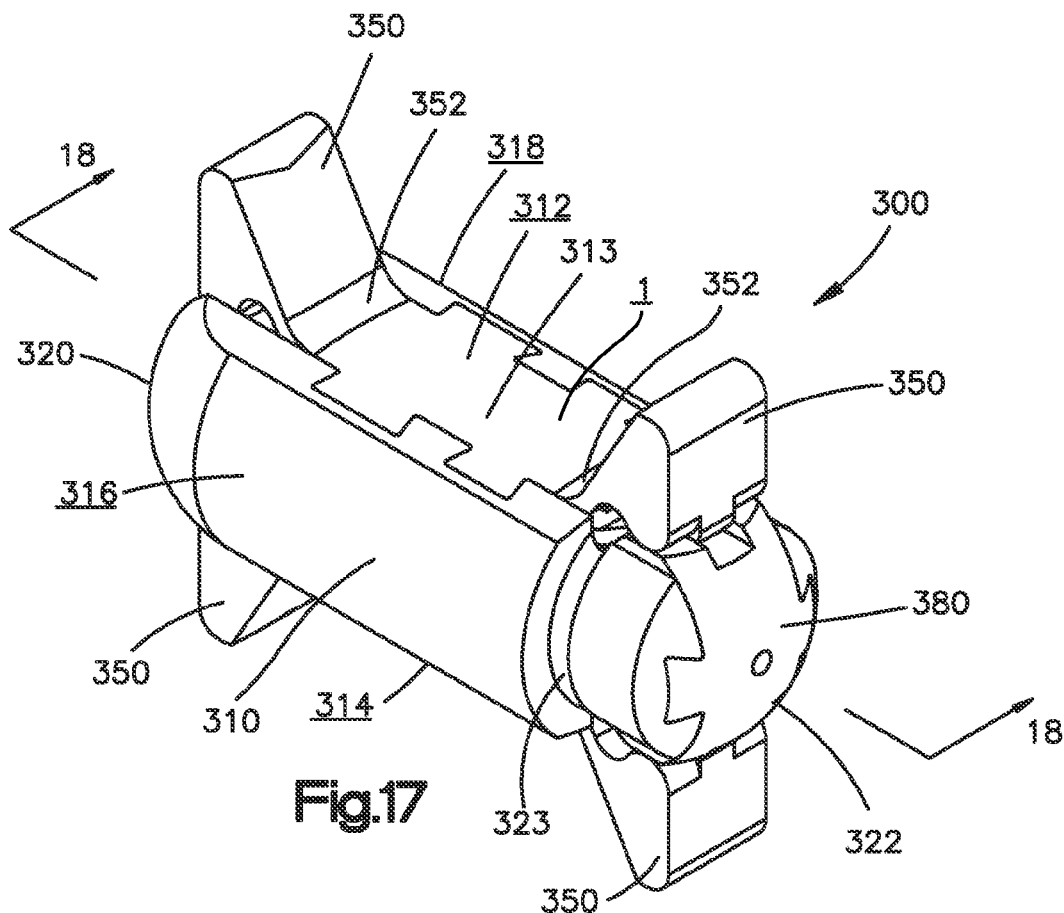
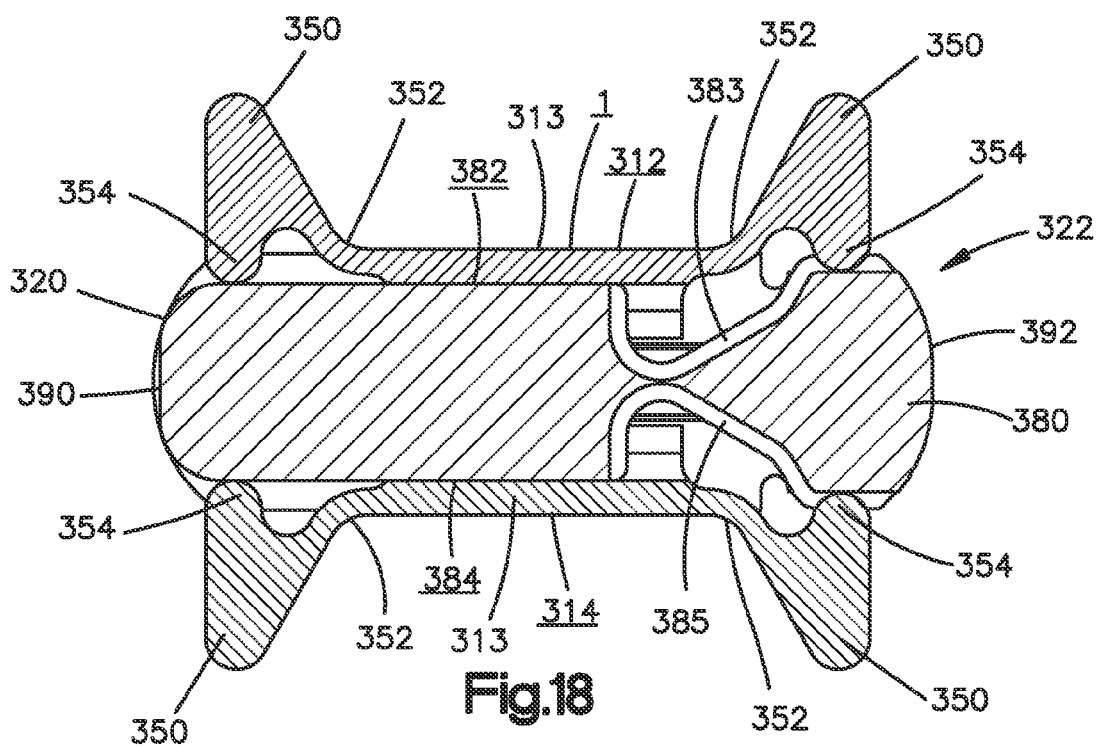

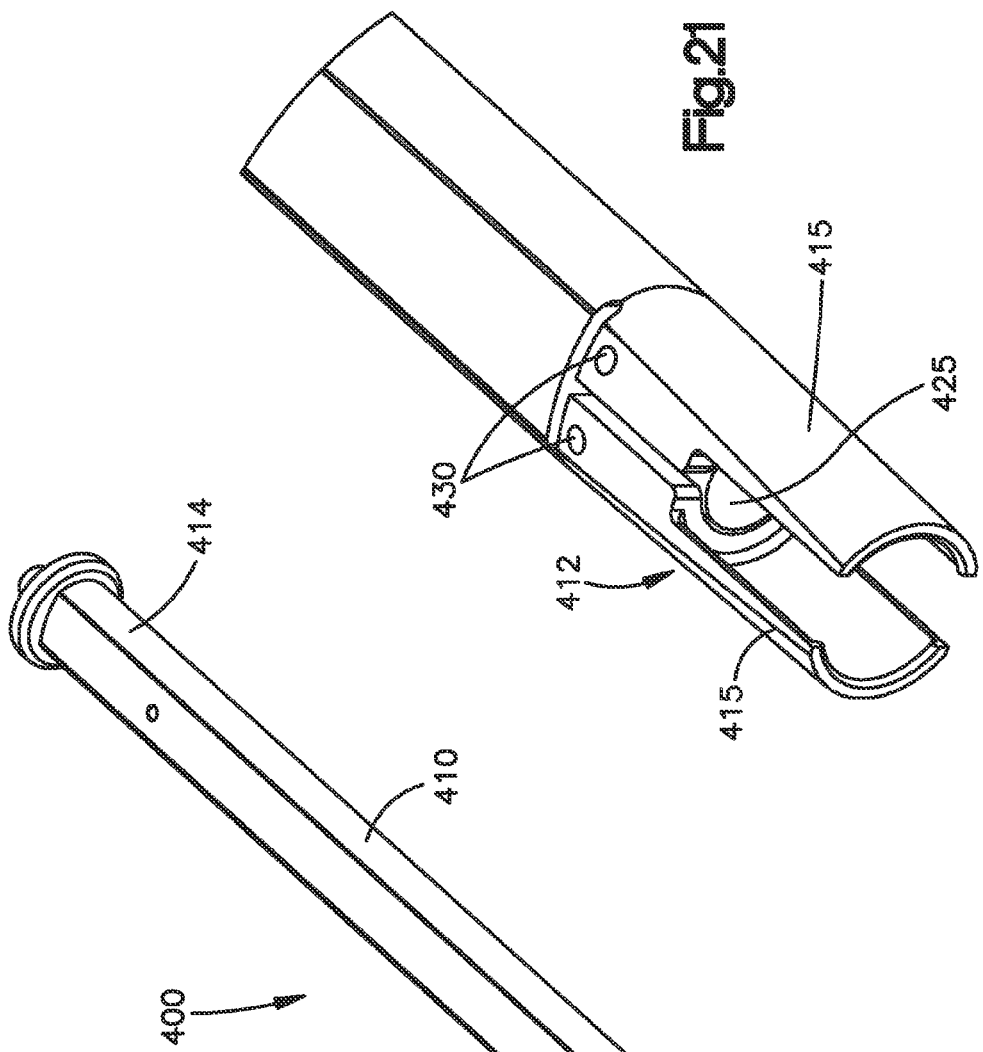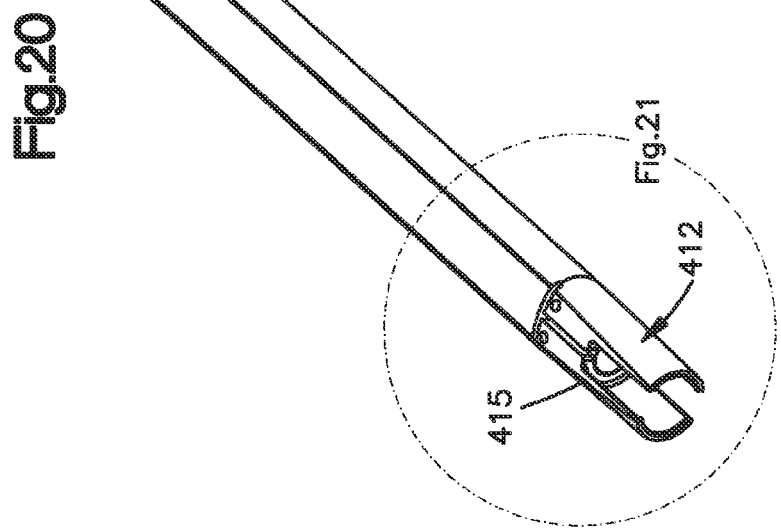

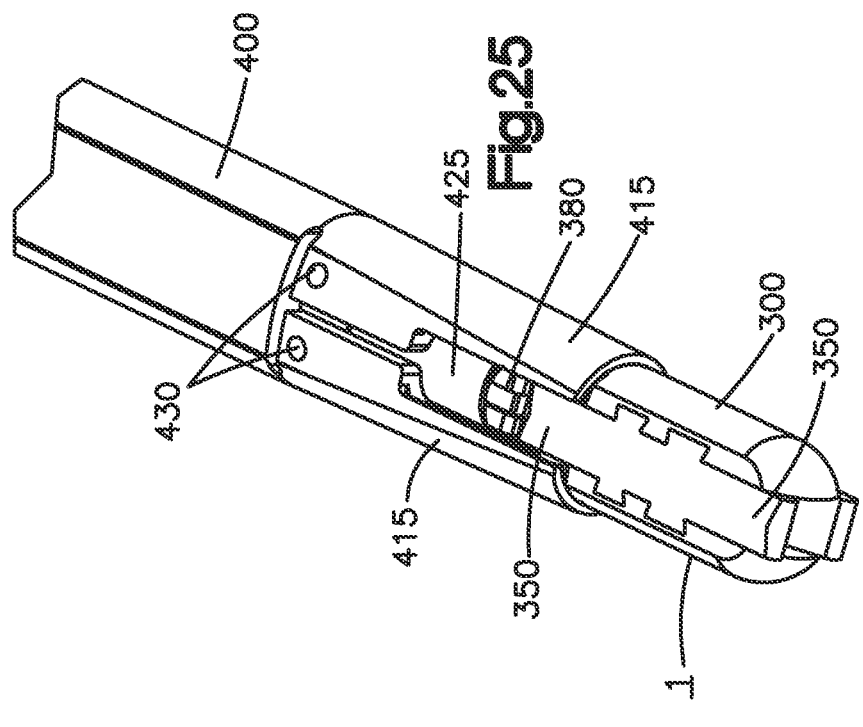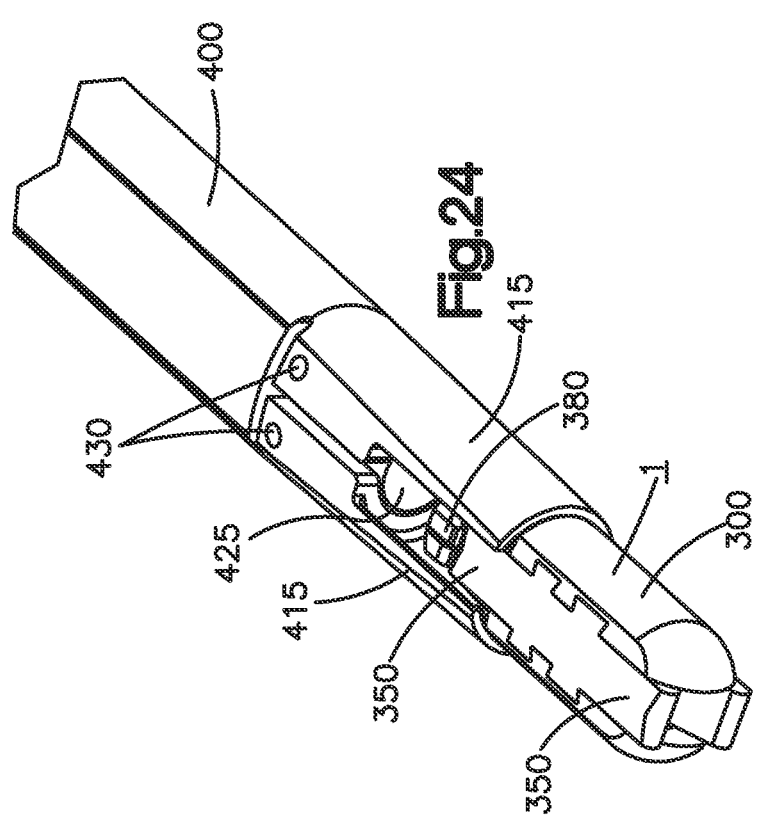

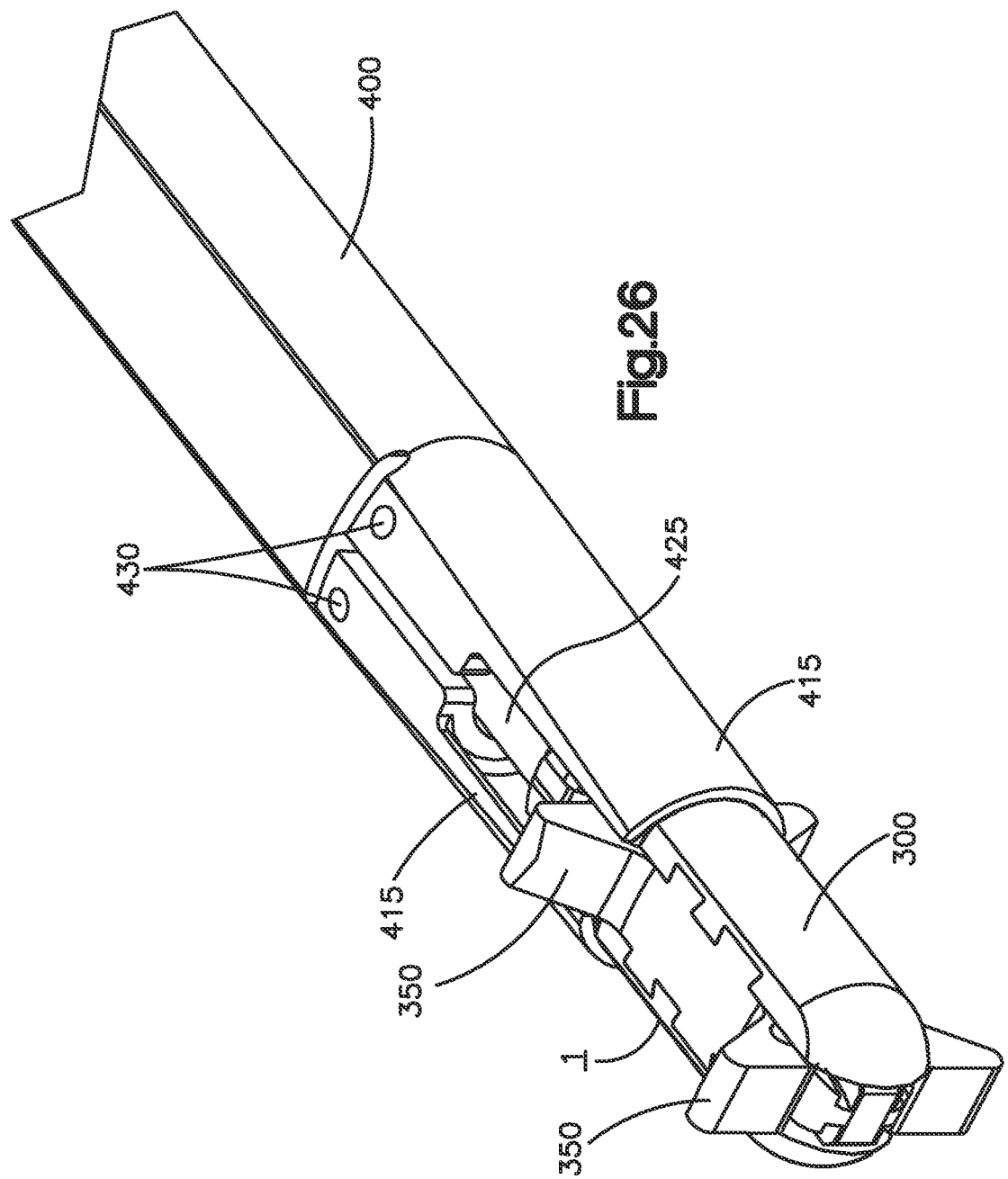

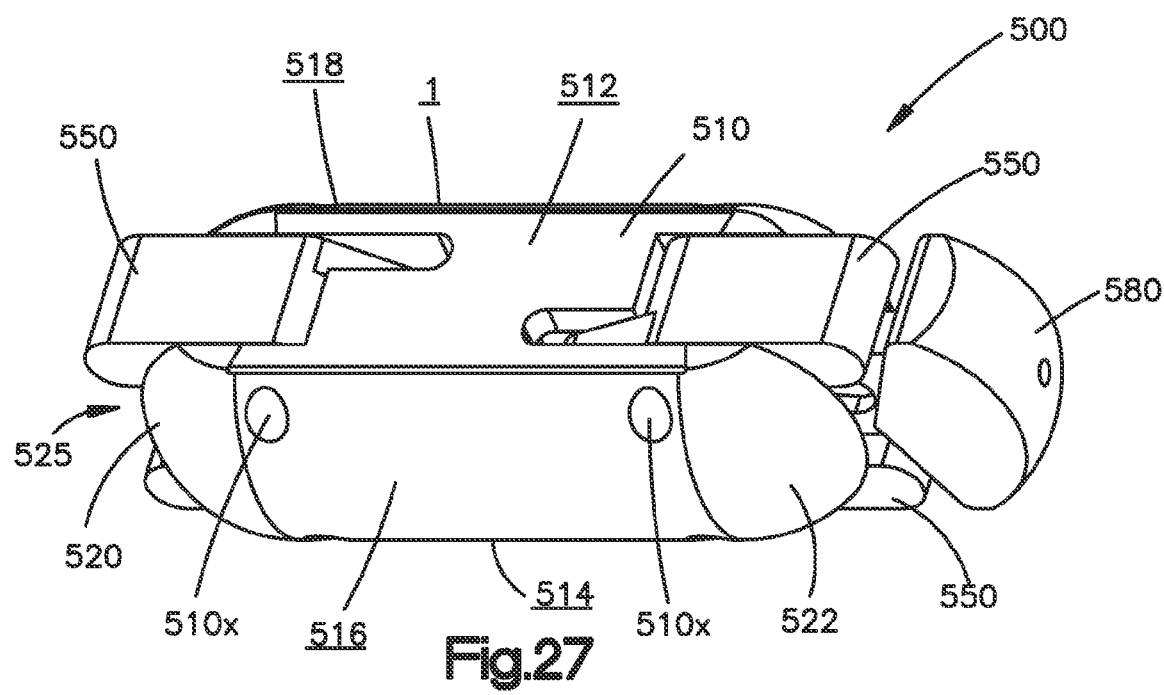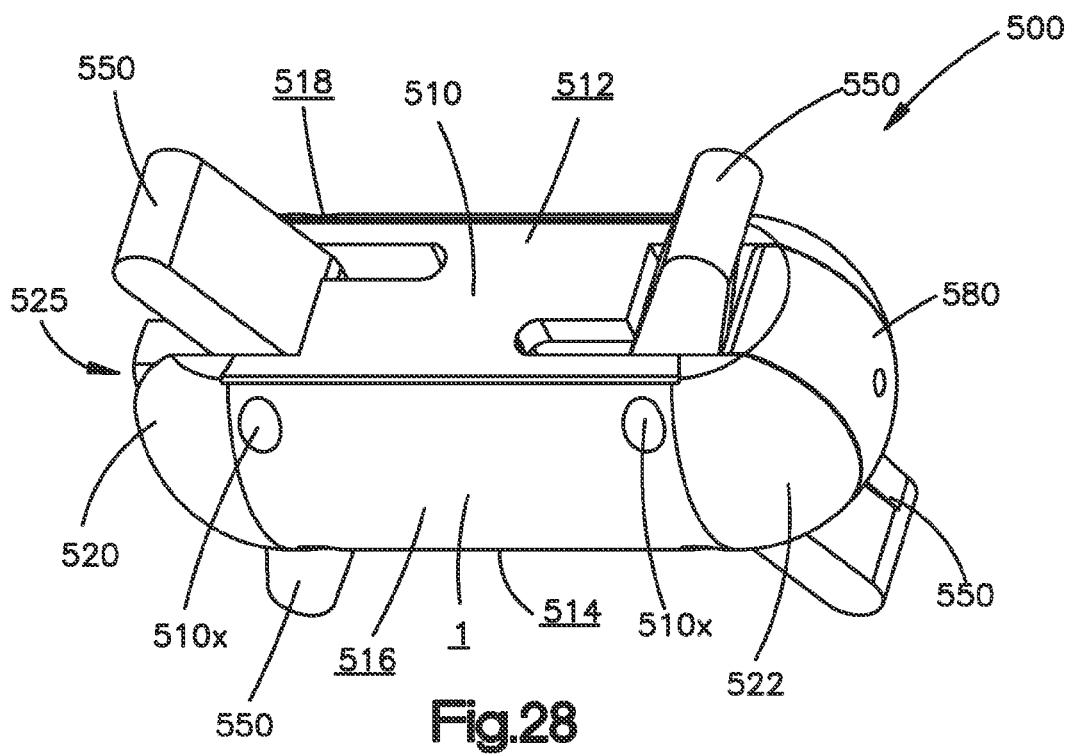

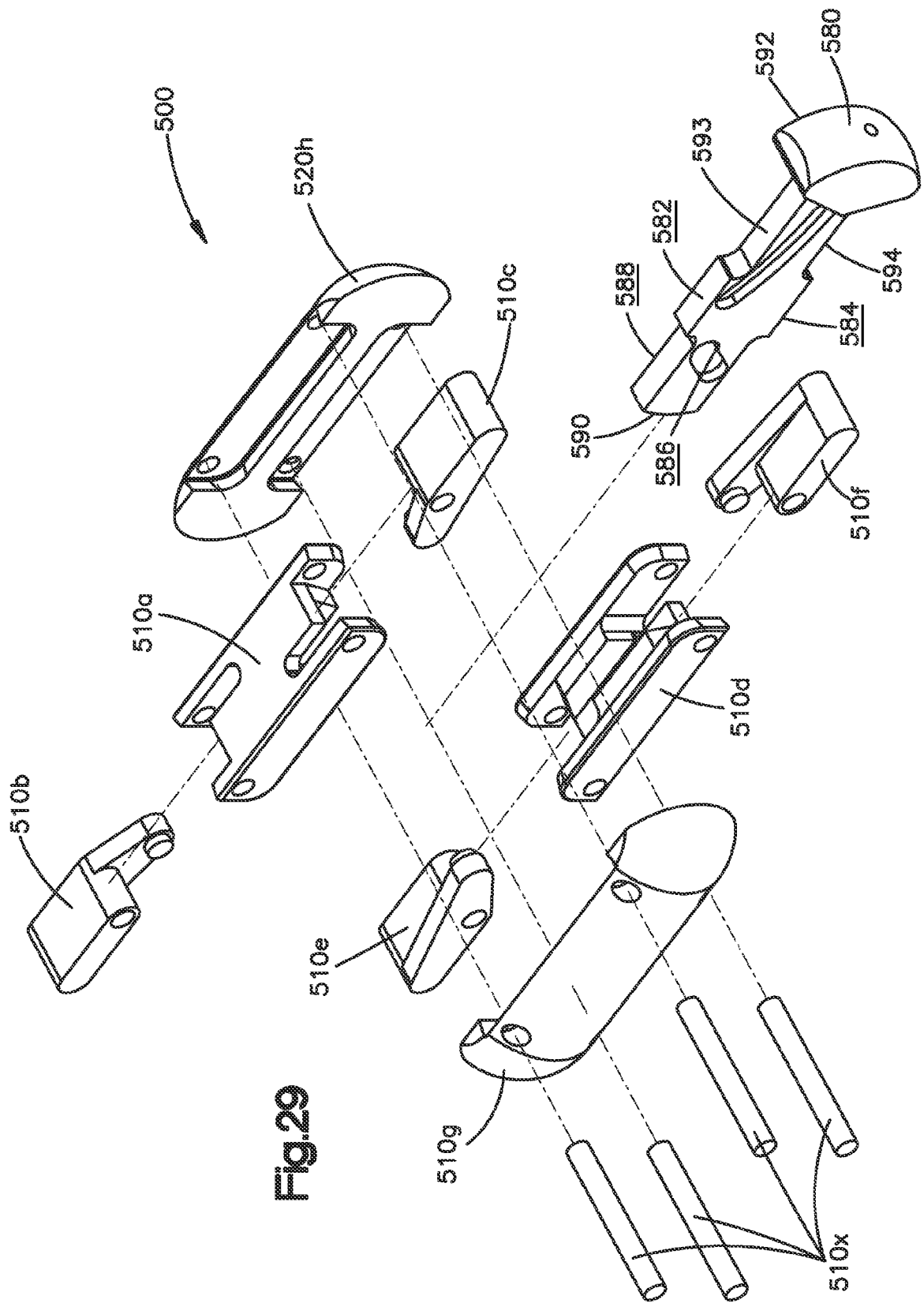

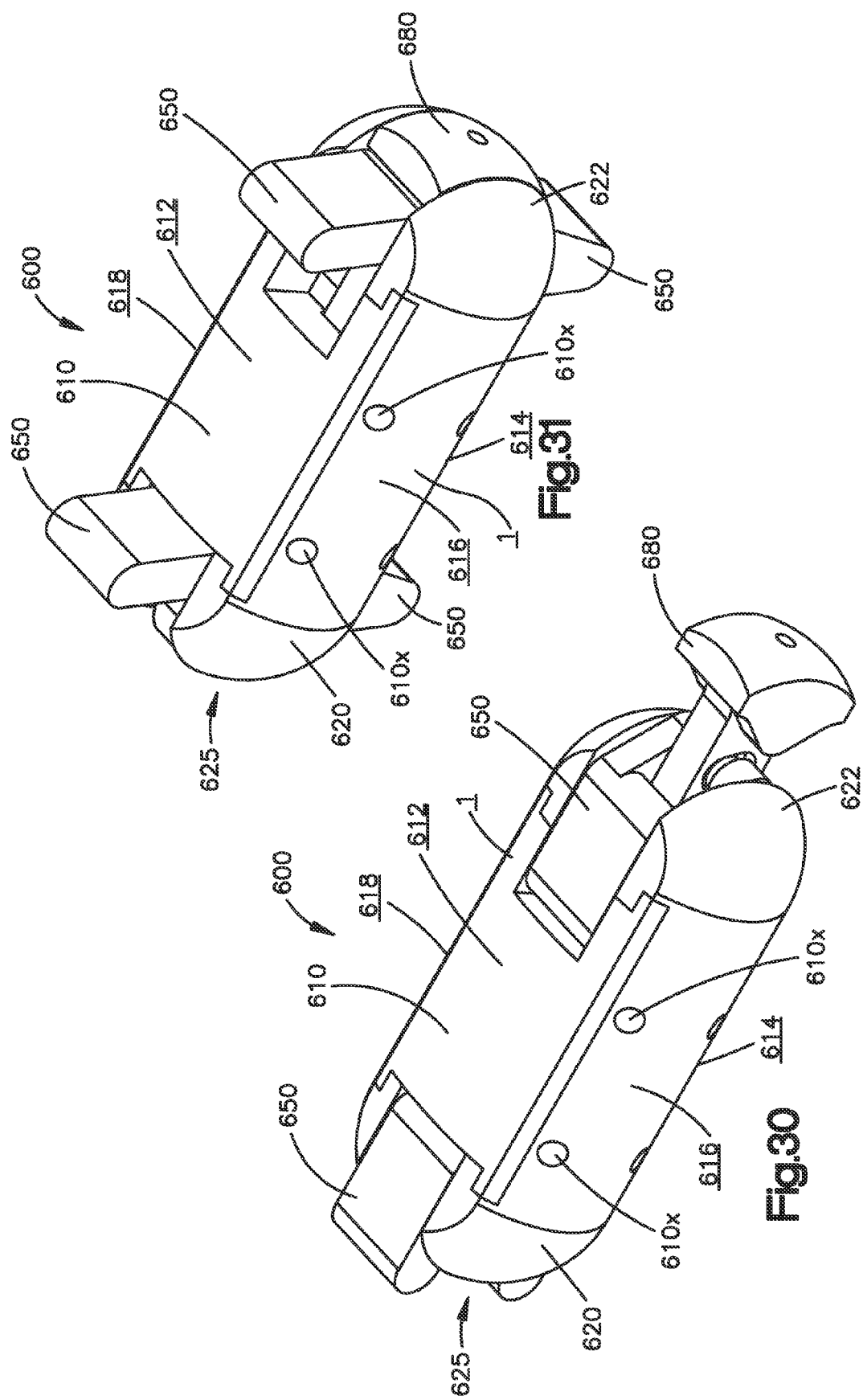

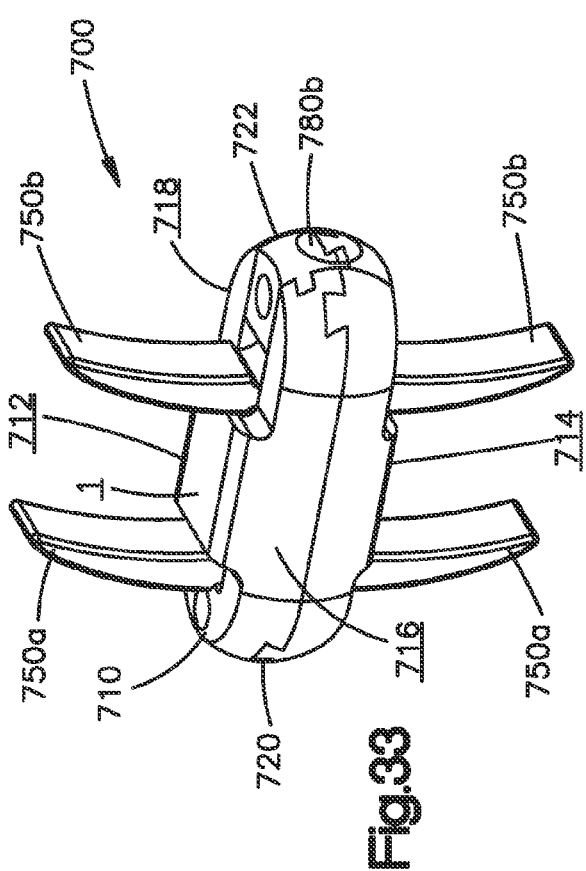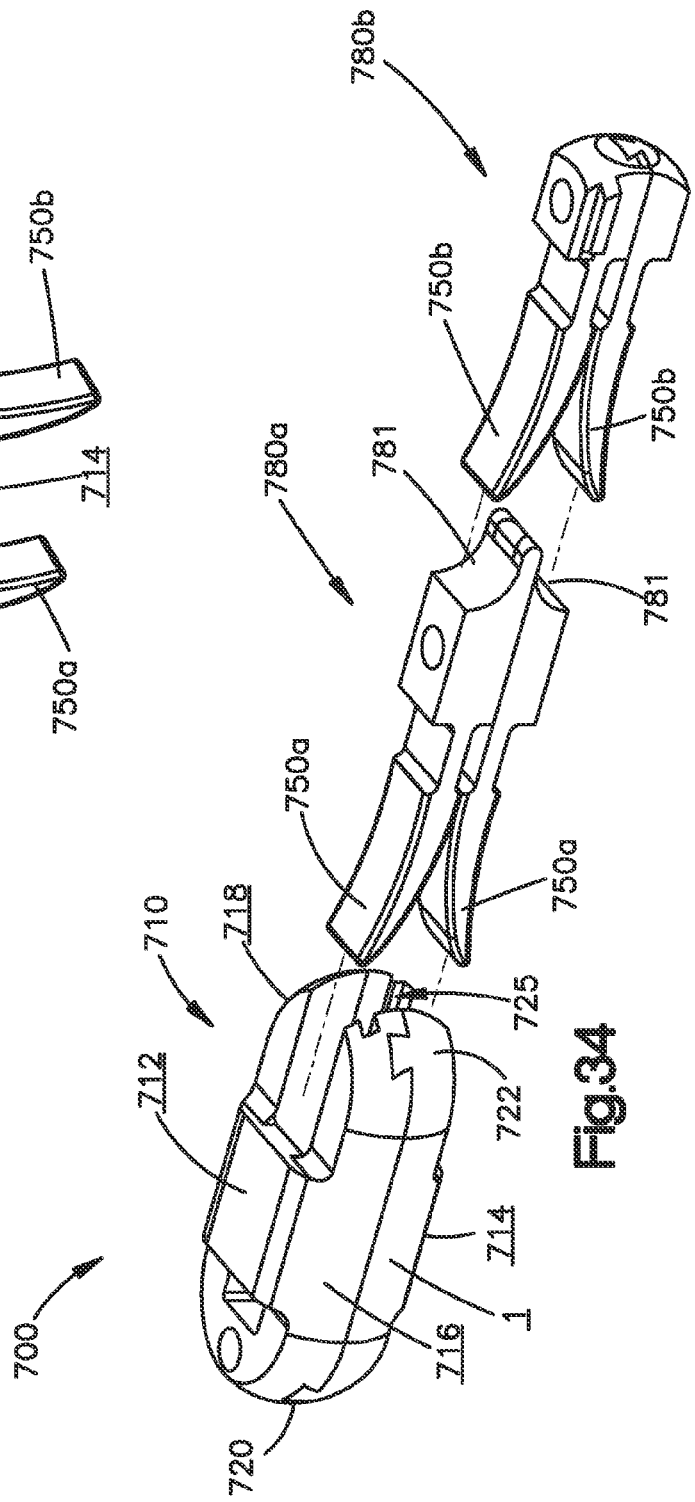

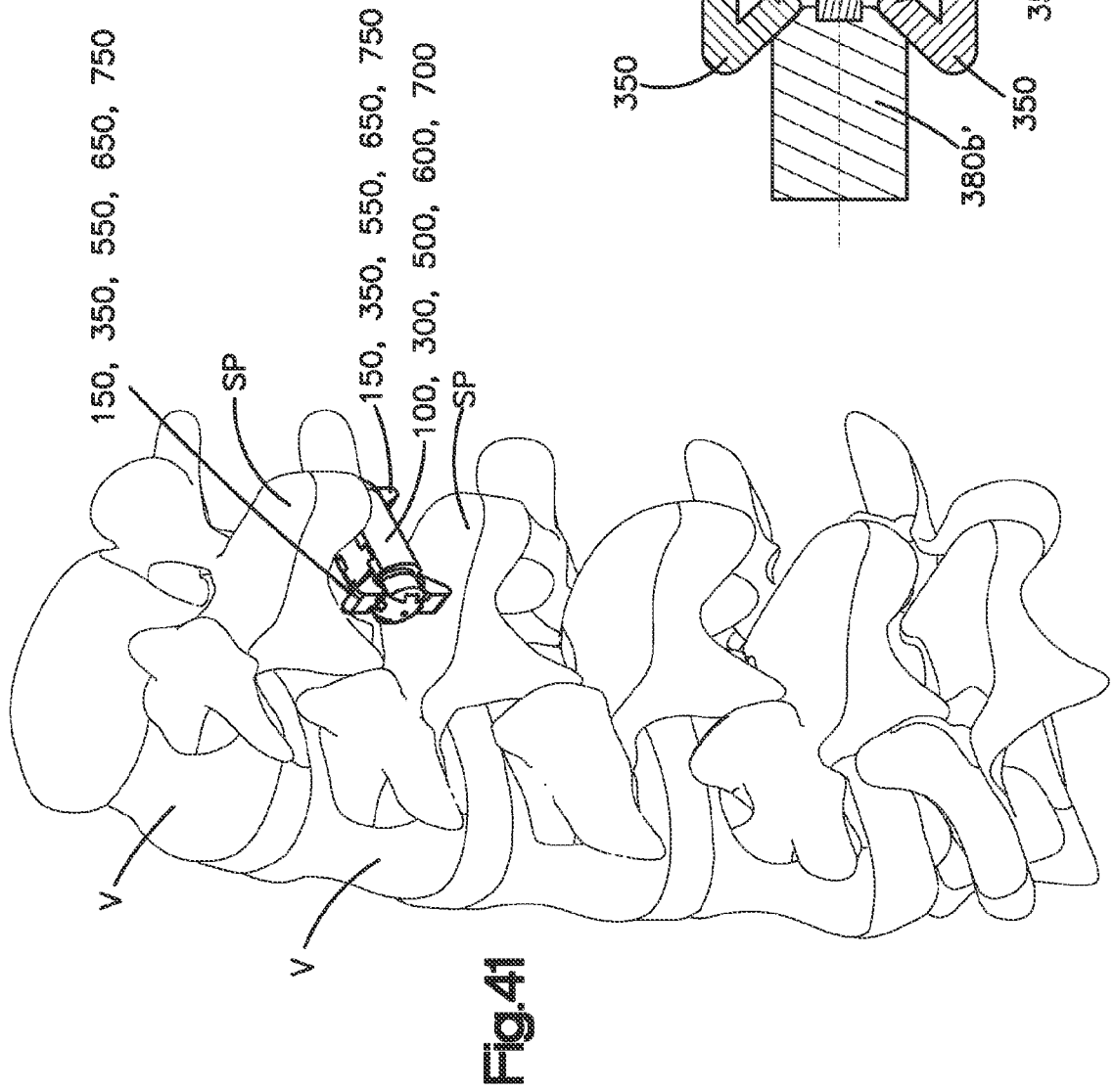

BONE-DERIVED SPACER ASSEMBLY

CROSS-REFERENCE TO RELATED APPLICATIONS

This application is the National Stage of International Application No. PCT/US2009/055428, filed Aug. 28, 2009, which claims the benefit of priority to U.S. Provisional Patent Application No. 61/092,655, filed Aug. 28, 2008, the disclosures of which are hereby incorporated by reference in their entireties.

BACKGROUND OF THE INVENTION

A human vertebra has a rearwardly projecting portion known as a spinous process. Bending of the spine can cause the spinous processes of adjacent vertebrae to move toward each other. This may, in some people, constrict the space in the spinal canal and foramina and, thus, may cause pain. Such constriction, which is known as stenosis, can be treated by the implantation of an interspinous spacer into the space between adjacent spinous processes.

Current interspinous spacers are typically constructed of separate pieces which require insertion from opposite sides of the spine, in a posterior approach, and necessitate rather large incisions, cutting both left and right thoracolumbar fascia as well as stripping the multifidus muscles from their attachments.

It is desirable to provide an interspinous spacer for implantation between spinous processes of adjacent vertebrae which can be laterally inserted in a first configuration through a single opening in a minimally invasive approach and which may then be deployed to a second configuration to maintain the spacer in position between the adjacent spinous processes.

In addition, current interspinous spacers are typically constructed from a metallic material such as, for example, titanium or a titanium alloy, or a polymer. However, in some cases of fractured or otherwise damaged bones, bone grafts may be used to repair or otherwise treat a damaged area. In the United States alone, approximately half a million bone grafting procedures are performed annually, directed to a diverse array of medical interventions for complications such as fractures involving bone loss, injuries or other conditions necessitating immobilization by fusion (such as for the spine or joints), and other bone defects that may be present due to trauma, infection, or disease. Bone grafting involves the surgical transplantation of pieces of bone within the body, and generally is effectuated through the use of graft material acquired from a human source. Human graft material is primarily utilized due to the limited applicability of xenografts, e.g., transplants from another species.

Some orthopedic procedures involve the use of allografts, which are bone grafts from other human sources (normally cadavers). Allografts, for example, are placed in a host bone and serve as the substructure for supporting new bone tissue growth from the host bone.

Manufacturing a bone-derived spacer however has its difficulties. For example, the various bones of the human body such as the femur (thigh), tibia and fibula (leg), humerus (upper arm), radius and ulna (lower arm) have geometries that vary considerably. The lengths of these bones are varied, as well as the shape of the cross section of each type of bone and the shape of any given bone over its length. In addition, the wall thickness may vary in different areas of the cross-section of each bone. Thus, the use of any given bone to produce a spacer or a component of a spacer may be a function of the donor bone's dimensions and geometry. Machining of bones, however, may permit the production of a spacer or a component of a spacer with standardized or custom dimensions.

Thus, it is desirable to provide a safe and effective interspinous spacer that can be manufactured from bone, laterally insertable via a minimally invasive surgical technique and once positioned, deployable to maintain the interspinous spacer in position.

BRIEF SUMMARY OF THE INVENTION

The present invention relates generally to an interspinous spacer. More specifically, the present invention relates to a deployable, bone-derived (e.g., allograft) interspinous spacer and associated system and method for laterally implanting the spacer into an interspinous space between the spinous processes of adjacent vertebrae.

The preferred embodiments of the present invention are directed to an allograft interspinous spacer for implantation into an interspinous space located between spinous process of adjacent vertebrae. The spacer preferably includes a body, a core and a plurality of deployable retainers. The body may be operatively associated with the plurality of deployable retainers. In use, after the body has been inserted into the interspinous space, the plurality of retainers is deployed so that they prevent migration of the spacer. The core is preferably sized and configured to be inserted and/or moved into operative engagement with the body to deploy the plurality of retainers. Preferably the spacer is manufactured from bone.

In one exemplary embodiment, the interspinous spacer includes a body, a core and a plurality of deployable retainers. The body includes a top bone contacting surface, a bottom bone contacting surface, a first side surface, a second side surface, a leading end, a trailing end and a bore extending from the trailing end. The plurality of deployable retainers is operatively associated with the top and bottom bone contacting surfaces of the body. The core includes a top surface, a bottom surface, a first side surface, a second side surface, a leading end and a trailing end. The core is slidably receivable within the bore formed in the body. In use, the body is sized and configured for implantation into the interspinous space with the plurality of retainers in a first, insertion configuration. The core is then inserted into the bore formed in the body, which in turn causes the retainers to deploy to a second, deployed configuration such that the retainers extend from the top and bottom bone contacting surfaces of the body, respectively, and adjacent to the spinous processes to maintain a position of the spacer. The spacer is preferably manufactured from bone.

In another exemplary embodiment, the core may be pre-inserted into the bore formed in the body prior to the body being inserted into the interspinous space. In this embodiment, the core is moveable between a first position and a second position, in the first position the plurality of retainers are in their first, insertion configuration and in the second position, the plurality of retainers are in their second, deployed configuration. For example, the core may include one or more recesses extending from the top and bottom surfaces of the core so that in the first position projections formed on the retainers align with the recesses formed in the core. Thereafter movement of the core to its second position causes the core to contact the projections formed on the retainers, thereby deploying the retainers to their second, deployed configuration.

The plurality of deployable retainers are preferably formed by demineralizing at least a portion of the top and bottom bone contacting surfaces so that end portions of the top and bottom contacting surfaces are moveable with respect to a central portion of the top and bottom bone contacting surfaces. Alternatively, the deployable retainers may be coupled to the body by one or more pins so that the retainers are hingeably coupled to the body.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating the interspinous spacer of the present application, there is shown in the drawings preferred embodiments. It should be understood, however, that the application is not limited to the precise arrangements and instrumentalities shown. In the drawings:

FIG. 1A is a side perspective view of a first preferred embodiment of an interspinous spacer according to the present invention, the spacer being shown in a second, deployed configuration;

FIG. 1B is a cross-sectional view of the interspinous spacer shown in FIG. 1A, taken along line 1B-1B in FIG. 1A;

FIG. 2 is a partially exploded view of the interspinous spacer shown in FIG. 1A illustrating a core member of the spacer being inserted in a body member of the spacer;

FIG. 3 is a partially exploded view of the interspinous spacer of FIG. 1A having a second preferred core member, the core member being insertable in the body member;

FIG. 3A is a detailed view of a core locking mechanism incorporated into the core of the interspinous spacer shown in FIG. 3;

FIG. 4 is an exploded view of a body assembly of the interspinous spacer shown in FIG. 1A;

FIG. 5 is a side perspective view of the body assembly of the interspinous spacer shown in FIG. 1A, the body incorporating an engagement feature for mating with a body insertion instrument;

FIG. 6 is a side perspective, fragmentary view of the body assembly shown in FIG. 5, the body assembly being coupled to an exemplary body insertion instrument;

FIG. 10 is a side perspective view of the core assembly of the interspinous spacer shown in FIG. 1A, the core incorporating an engagement feature for mating with a core insertion instrument;

FIG. 11 is a side perspective fragmentary view of the core shown in FIG. 10 coupled to an exemplary core insertion instrument;

FIG. 17 is a side perspective view of the interspinous spacer shown in FIG. 15, the spacer being shown in a second, deployed configuration;

FIG. 18 is a cross-sectional view of the interspinous spacer shown in FIG. 17, taken along line 18-18 in FIG. 17;

FIG. 20 is a side perspective view of an insertion instrument for use with the interspinous spacer shown in FIG. 15;

FIG. 21 is a detailed view of a distal end of the insertion instrument shown in FIG. 20;

FIGS. 24-26 are detailed, perspective views of the insertion instrument shown in FIG. 20, the insertion instrument coupling to and deploying the spacer shown in FIG. 15;

FIG. 27 is a side perspective view of a third preferred embodiment of an interspinous spacer according to the present invention, the spacer being shown in a first, insertion configuration;

FIG. 28 is a side perspective view of the interspinous spacer shown in FIG. 27, the spacer being shown in a second, deployed configuration;

FIG. 29 is an exploded view of the spacer shown in FIG. 27;

FIG. 30 is a top perspective view of a fourth preferred embodiment of an interspinous spacer according to the present invention, the spacer being shown in a first, insertion configuration;

FIG. 31 is a top perspective view of the interspinous spacer shown in FIG. 30, the spacer being shown in a second, deployed configuration;

FIG. 33 is a side perspective view of a fifth preferred embodiment of an interspinous spacer according to the present invention, the spacer being shown in a second, deployed configuration;

FIG. 34 is a partially exploded, side perspective view of the spacer shown in FIG. 33 illustrating the core members being inserted into the body member;

FIGS. 35-41 are side perspective views illustrating the steps of one exemplary method of implanting the interspinous spacer shown in FIG. 15; and FIG. 42 is a cross-sectional view of an alternate embodiment of the core member that may be used with the spacer shown in FIGS. 15 and 27.

DETAILED DESCRIPTION OF THE INVENTION

Figure 7:
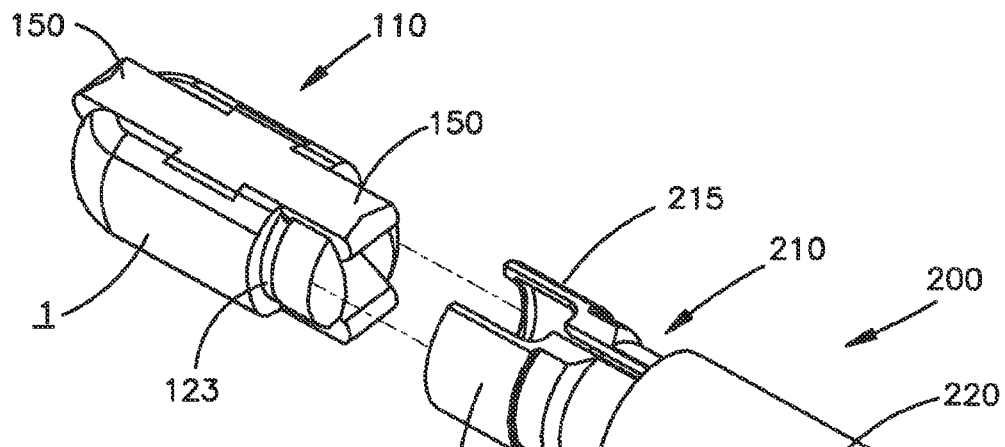
FIGS. 7-9 are detailed, side perspective views of the body insertion instrument shown in FIG. 6 coupling to the body assembly shown in FIG. 5.
Figure 8:
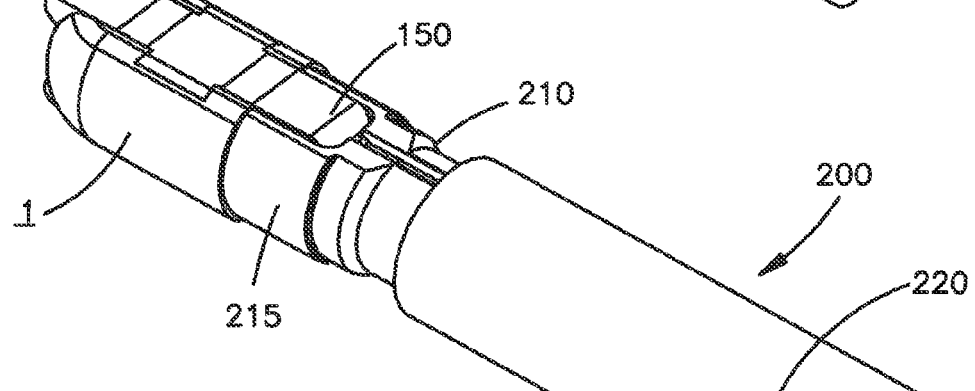
Figure 9:
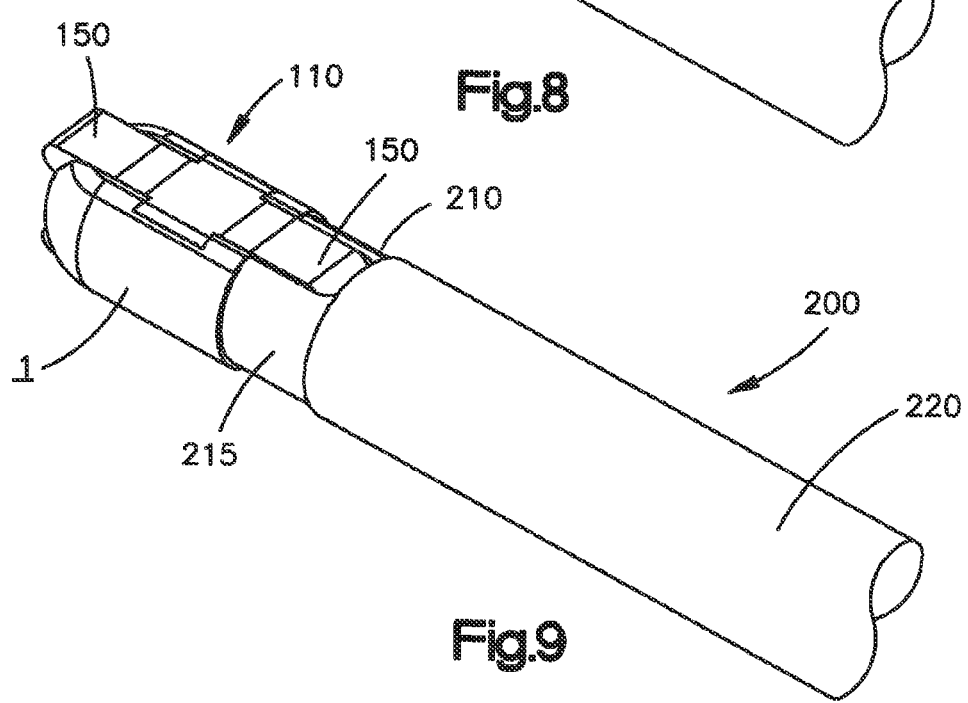
Figure 12:
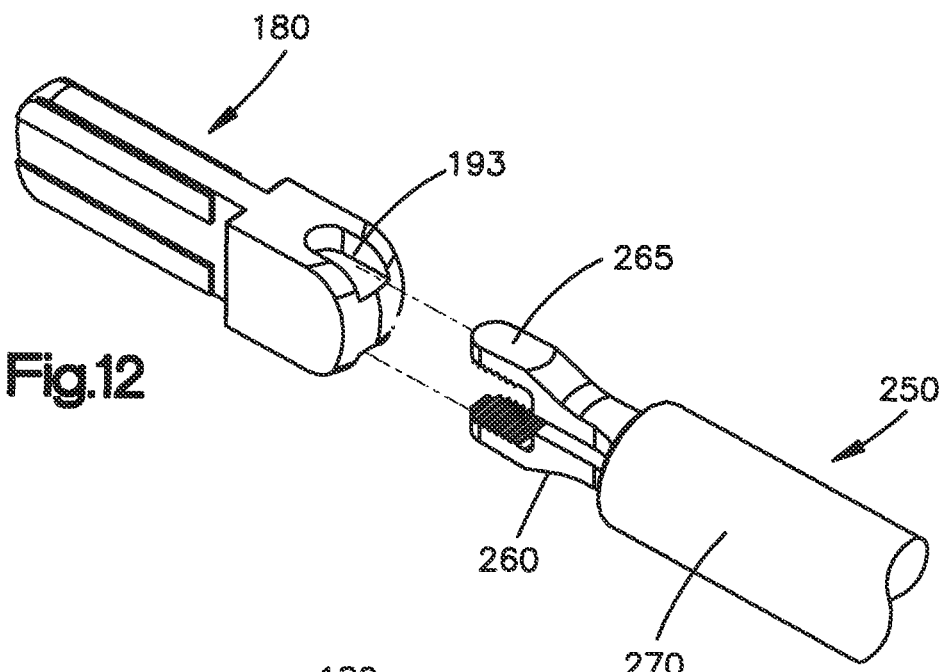
FIGS. 12-14 are detailed, perspective views of the core insertion instrument shown in FIG. 11 coupling to the core shown in FIG. 10.
Figure 13:
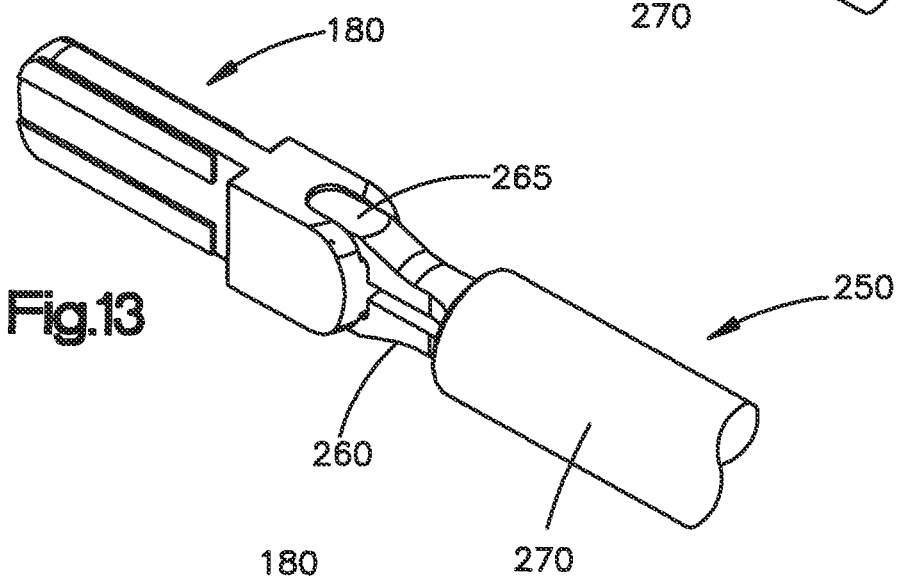
Figure 14:
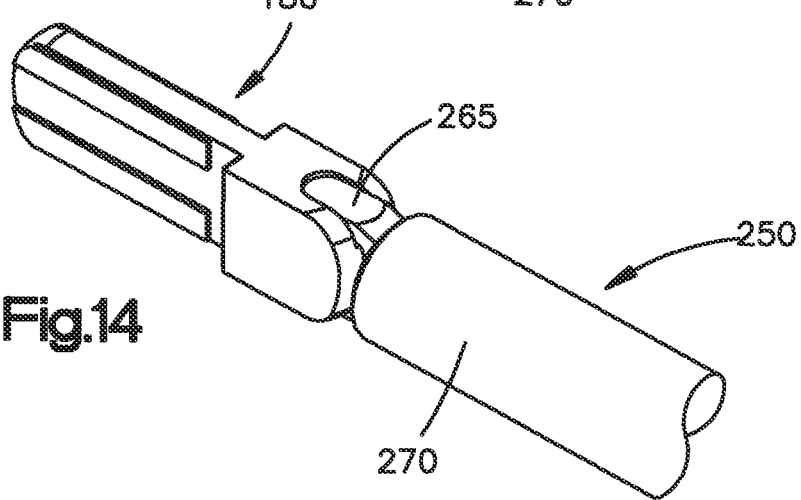

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the interspinous spacer and related parts thereof. The words, "anterior", "posterior", "superior", "inferior", "lateral" and related words and/or phrases designate preferred positions and orientations in the human body to which reference is made and are not meant to be limiting. The terminology includes the above-listed words, derivatives thereof and words of similar import.

Certain exemplary embodiments of the invention will now be described with reference to the drawings. In general, such embodiments relate to first, second, third, fourth and fifth preferred embodiments of an interspinous spacer 100, 300, 500, 600, 700 by way of non-limiting example, an interspinous spacer 100, 300, 500, 600, 700 for insertion into an interspinous space between adjacent spinous processes Sp. The invention may have other applications and uses and should not be limited to the structure or use described and illustrated.

As will be described in greater detail below, the interspinous spacer 100, 300, 500, 600, 700 preferably includes a body member 110, 310, 510, 610, 710, a core 180, 180', 380, 380', 580, 680, 780 and a plurality of deployable retainers 150, 350, 550, 650, 750. The body member 110, 310, 510, 610, 710 may be operatively associated with the plurality of deployable retainers 150, 350, 550, 650, 750. The body member 110, 310, 510, 610, 710 is sized and configured for implantation into an interspinous space located between the spinous process Sp of adjacent superior and inferior vertebrae V. In use, after the body member 110, 310, 510, 610, 710 has been inserted into the interspinous space between adjacent spinous processes Sp, the plurality of retainers 150, 350, 550, 650, 750 may be deployed so that they extend from the body 110, 310, 510, 610, 710 for contacting the sides of the adjacent spinous processes Sp to prevent migration of the spacer 100, 300, 500, 600, 700. The core 180, 180', 380, 380', 580, 680, 780 is preferably sized and configured to be inserted and/or moved into operative engagement with the body 110, 310, 510, 610 to deploy the plurality of retainers 150, 350, 550, 650, 750, as will be described in greater detail below.

Referring to FIGS. 1A-14, a first preferred embodiment of the interspinous spacer 100 includes a body member 110 and a core 180. The body member 110 is operatively associated with a plurality of deployable retainers 150 and has a bore 125 for receiving the core 180.

The interspinous spacer 100 including the body 110, retainers 150 and core 180, will be described as and is preferably manufactured from bone (e.g., allograft bone), unless otherwise indicated. Manufacturing the interspinous spacer 100 from bone helps facilitate fusion of the spacer 100 to one or both of the adjacent spinous processes Sp. However it is envisioned that one or more components of the first preferred interspinous spacer 100 may be manufactured from another biocompatible material such as, for example, metal (e.g., stainless steel, titanium, aluminum, an alloy of two or more metals), polymer such as, for example, PEEK, plastic, rubber, ceramic, or a composite material (i.e., made up of two or more materials). Depending on the material used, the spacer 100 may incorporate one or more radio-opaque markers to assist a surgeon in properly aligning the body 110 or other components relative to a patient's anatomy.

The first preferred embodiment of the body 110 is sized and configured for positioning in the interspinous space between spinous processes Sp of adjacent vertebrae V for treating, for example, spinal stenosis. The body 110 includes a top bone contacting surface 112, a bottom bone contacting surface 114, a first side surface 116, a second side surface 118, a leading end 120 and a trailing end 122. The body 110 may be any shape, for example, round, polygonal, square, etc. Preferably, the body 110 has an oblong shape for insertion into the interspinous space via a generally minimally invasive incision. The top and bottom bone contacting surfaces 112, 114 may be smooth or rough (e.g. toothed or ridged) and/or flat or radiused (i.e. cylindrical), as generally shown. Alternatively, the top and bottom bone contacting surfaces 112, 114 may include a notch or trough, commonly referred to as a seat (not shown), for receiving and mating with the adjacent spinous processes Sp and for positioning the body 110 in a preferred orientation relative to the adjacent spinous processes Sp. The trailing end 122 preferably includes one or more engagement features 123 for mating with a body insertion instrument 200 for inserting the body 110 between the adjacent spinous processes Sp, as will be described in greater detail below. The body 110 further includes a bore 125 extending from the trailing end 122 for receiving the core 180 for reasons that will become apparent below. The bore 125 may extend partially or completely through the body 110 to the leading end 120.

The core 180 is sized and configured for insertion into the bore 125 formed in the body 110. The core 180 includes a top surface 182, a bottom surface 184, a first side surface 186, a second side surface 188, a leading end 190 and a trailing end 192. The core 180 may be any shape, for example, round, polygonal, square, etc. Preferably the core 180 has an oblong shape. The trailing end 192 preferably includes one or more engagement features 193 for mating with a core insertion instrument 250 for inserting the core 180 into the bore 125 formed in the body 110, as will be described in greater detail below.

The body 110 and/or core 180 may be machined from a single piece of bone or may be machined from a plurality of bone pieces that are connected to one another via an attachment mechanism, such as, for example, dovetails, pins, opposing taper locks, allograft welding, etc. Referring to FIG. 4, for example, it is envisioned that the body 110 of the first preferred embodiment may be manufactured from a total of six parts including a top part 110a, a bottom part 110b, a top left side 110c, a bottom left side 110d, a top right side 110e and a bottom right side 110f, although the body 110 may be manufactured from more or less parts including, but not limited to, two, three, four, seven, eight, etc. The various parts are preferably interconnected via interlocking projections 110g and recesses 110h that may be adhesively bonded, allograft welded or otherwise secured together. As generally illustrated in FIG. 3, the core 180 may be manufactured from two parts including a top part 180a and a bottom part 180b, although the core 180 may be manufactured from more or less parts including, but not limited to, one, three, four, etc. parts.

Referring to FIGS. 1-14, the body 110 preferably includes deployable retainers 150 on both the top and bottom bone contacting surfaces 112, 114 to assist in securing the spacer 100 between the adjacent spinous processes Sp. The deployable retainers 150 are preferably manufactured by demineralizing at least portions of the top and bottom contacting surfaces 112, 114 and into the thickness of the top part 110a, the bottom part 110b so that the top and bottom parts 110a, 110b include hinges 152 between a central portion 113 and the flexible deployable retainers 150. The hinges 152 of the first preferred embodiment are preferably living hinges that separate the retainers 150 from the central portion 113 and permit the retainers 152 to move, preferably pivot, relative to the central portion 113. The interspinous spacer 100 including the body 110 and the retainers 150 may be demineralized to some level, as it is believed that the demineralizing process helps promote fusion between the spacer 100 and the adjacent spinous processes SP. However, it is envisioned that only the hinges 152 will undergo sufficient demineralization to render them flexible to an extent to permit the retainers 150 to flex between a first, insertion position and a second, deployed position. Alternatively, it is envisioned that only the hinges 152 or the entire top and bottom bone contacting surfaces 112, 114 of the body 110 may be demineralized and thus flexible based on the demineralization process parameters (time of demineralization, acid concentration, use of masks, etc.). By sufficiently demeralizing the hinges 152 to render them flexible, the retainers 150 become moveable and/or pivotable relative to the central portion 113. In this manner, the deployable retainers 150 are integrally formed with the top and bottom parts 110a, 110b such that the body 110 may be inserted into the interspinous space with the retainers 150 in the first, insertion position (as generally shown in FIGS. 2 and 3). Once the body 110 has been positioned in the interspinous space, the retainers 150 are deployable to the second, deployed position (as generally shown in FIGS. 1A and 1B) to prevent migration of the spacer 100 (i.e., to limit movement of the interspinous spacer 100 relative to the patient's spinous processes Sp). In the deployed position, the retainers 150 preferably extend from the top and bottom bone contacting surfaces 112, 114 and are located on either side of the spinous processes Sp between which the interspinous spacer 100 is positioned.

More preferably, the retainers 150 are deployed by insertion of the core 180 into the bore 125 formed in the body 110 of the spacer 100. That is, as best shown in FIGS. 1B, 2 and 3, each of the deployable retainers 150 includes a projection 154 protruding into the bore 125 of the body 110 such that insertion of the core 180 into the bore 125 contacts and moves the projections 154 radially out of the bore 125, which in turn causes the retainers 150 to move from their first, insertion configuration to their second, deployed configuration.

Referring to FIGS. 3 and 3A, a second exemplary embodiment of the core 180' is substantially identical to the first exemplary embodiment of the core 180, however, the second exemplary core 180' includes a core locking mechanism for securing the final position of the core 180' with respect to the body 110. For example, the top and bottom surfaces 182', 184' of the core 180' may include a recess 195' for mating with a leg 154a of the projections 154. The leg 154a extending from the projection 154 is preferably sized and configured so that once the core 180' is inserted into the bore 125 formed in the body 110, one or more of the legs 154a mate with one or more of the recesses 195' formed in the core 180' to limit or prevent backing out of the core 180' with respect to the body 110. Alternatively any other locking mechanism now or hereafter known in the art may be used, such as, for example, a sliding dovetail feature (not shown) that would serve to connect the core 180' to the body 110. The spacer 100 could include a locking interface between the core 180 and the body 110, the core 110 and the retainers 150 or both.

Referring to FIGS. 5-9, the body 110 preferably includes the engagement feature 123 for coupling to a body insertion instrument 200. The engagement feature 123 can be any feature and/or element now or hereafter known for such purpose. Preferably, the engagement feature 123 is comprised of a groove extending circumferentially around the first and second side surfaces 116, 118 adjacent to the trailing end 122 for engaging a plurality of fingers 215 extending from the body insertion instrument 200. More specifically, the body insertion instrument 200 preferably includes an inner sleeve 210 and an outer sleeve 220, wherein the inner sleeve 210 is moveably associated within the outer sleeve 220. The distal end of the inner sleeve 210 includes a plurality of fingers 215 for engaging the engagement feature 123 formed on the trailing end 122 of the body 110. The plurality of fingers 215 are preferably sized and configured to engage the body 110 without interfering with the deployable retainers 150 so that the core 180 can be inserted into the bore 125 formed in the body 110, as will be described in greater detail below, and the retainers 150 can be deployed while the body insertion instrument 200 engages the body 110. Once the body 110 has been positioned within the fingers 215 of the inner sleeve 210, the outer sleeve 220 is preferably moved distally with respect to the inner sleeve 210. Distal movement of the outer sleeve 220 with respect to the inner sleeve 210 prevents the fingers 215 formed on the inner sleeve 210 from radially expanding (e.g. spreading apart) and, thereby, prevents the dislodgement of the body 110 from the body insertion instrument 200.

Similarly, referring to FIGS. 10-14, the core 180 preferably includes an engagement feature 193 for coupling to a core insertion instrument 250. The engagement feature 193 can be any feature and/or element now or hereafter known for such purpose including, for example, a threaded interface for threadably engaging a threaded hole, a groove for receiving a ball detent, etc. Preferably, the engagement feature 193 is comprised of a pair of recesses formed in the top and bottom surfaces 182, 184 adjacent to the trailing end 192 for engaging a plurality of fingers 265 extending from the core insertion instrument 250. More specifically, the core insertion instrument 250 preferably includes an inner sleeve 260 and an outer sleeve 270, the inner sleeve 260 being moveably associated within the outer sleeve 270. The distal end of the inner sleeve 260 including a plurality of fingers 265 for engaging the recesses 193 formed on the trailing end 192 of the core 180. Once the core 180 has been positioned within the fingers 265 of the inner sleeve 260, the outer sleeve 270 is preferably moved distally with respect to the inner sleeve 260. Distal movement of the outer sleeve 270 with respect to the inner sleeve 260 prevents the fingers 265 formed on the inner sleeve 260 from radially expanding (e.g., spreading apart) and, thereby, prevents dislodgement of the core 180 from the core insertion instrument 250.

In use, the core insertion instrument 250 and the core 180 are sized and configured for insertion thru a cannulated bore formed in the body insertion instrument 200 so that, after the body 110 is implanted in the interspinous space between adjacent spinous processes Sp via the body insertion instrument 200, the surgeon can insert the core 180 through the cannulated bore formed in the body insertion instrument 200 and into the bore 125 formed in the body 110, thereby deploying the retainers 150 from their first, insertion configuration to their second, deployed configuration adjacent the spinous processes Sp.

Referring to FIGS. 15-19, a second preferred embodiment of the interspinous spacer 300 includes a body member 310 and a core 380. The body member 310 is operatively associated with a plurality of deployable retainers 350 and has a bore 325 for receiving the core 380. The second preferred interspinous spacer 300 is similar to the first preferred interspinous spacer 100 described above, as such the same reference numerals will be utilized to describe similar or the same components and the description will focus on the specific features of interspinous spacer 300 of the second preferred embodiment that distinguish it from interspinous spacer 100 of the first preferred embodiment.

The body 310 of the second preferred embodiment is sized and configured for positioning in the interspinous space between spinous processes Sp of adjacent vertebrae V. The body 310 includes a top bone contacting surface 312, a bottom bone contacting surface 314, a first side surface 316, a second side surface 318, a leading end 320 and a trailing end 322. The body 310 may be any shape, for example, round, polygonal, etc. Preferably the body 310 has an oblong shape. The trailing end 322 preferably includes one or more engagement features 323 for mating with an insertion instrument 400 for inserting the spacer 300 between the adjacent spinous processes Sp, as will be described in greater detail below. The body 310 further includes a bore 325 extending from the trailing end 322. The bore 325 may extend partially or completely through the body 310 to the leading end 320.

The core 380 is sized and configured for insertion into the bore 325 formed in the body 310. The core 380 includes a top surface 382, a bottom surface 384, a first side surface 386, a second side surface 388, a leading end 390 and a trailing end 392. The core 380 may be any shape, for example, round, polygonal, etc. Preferably the core 380 has an oblong shape.

Figure 19:
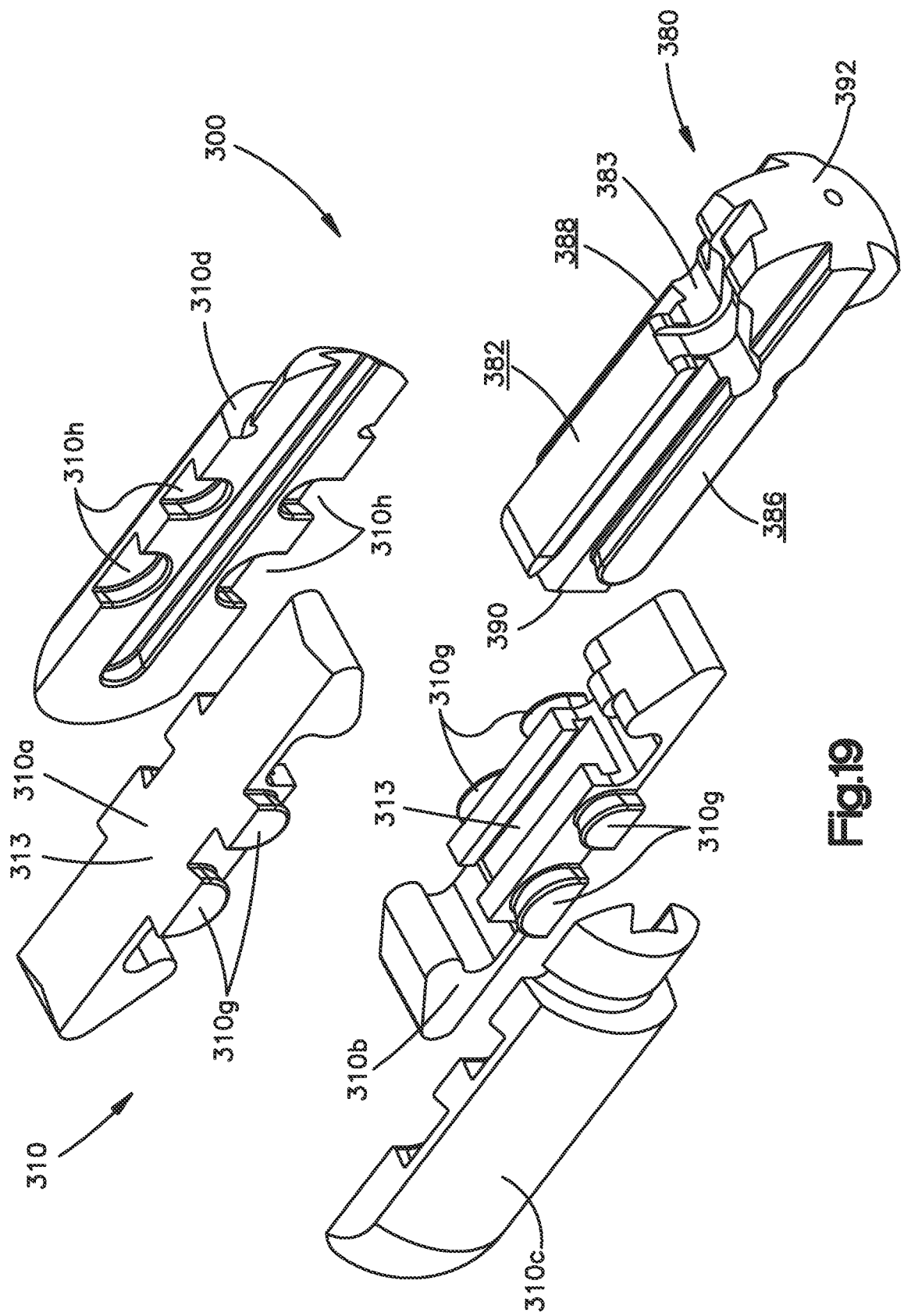
FIG. 19 is an exploded view of the spacer shown in FIG. 15.
Figure 22:
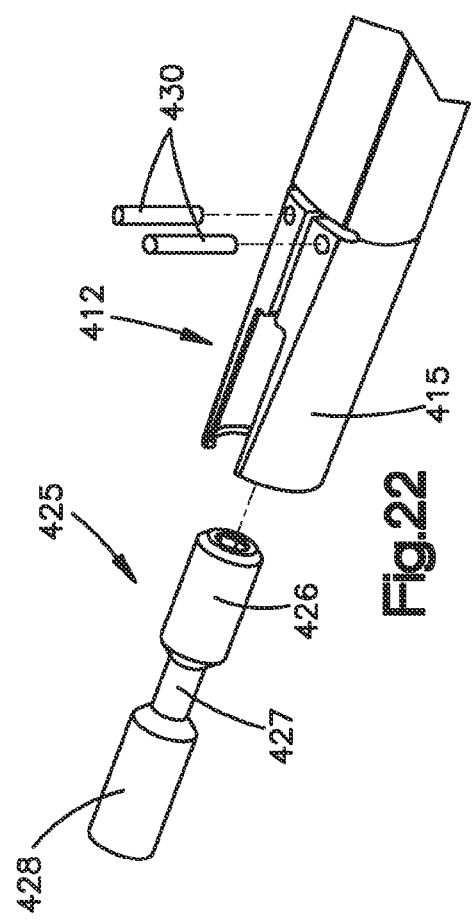
FIG. 22 is an exploded view of the distal end of the insertion instrument shown in FIG. 20.

The body 310 and/or the core 380 may be machined from a single piece of bone or may be machined from a plurality of bone pieces that are connected to one another via an attachment mechanisms, such as, for example, dovetails, pins, opposing taper locks, allograft welding, etc. Referring to FIG. 19, for example, it is envisioned that the body 310 may be manufactured from a total of four parts including a top part 310a, a bottom part 310b, a left side 310c and a right side 310d, although the body 310 may be manufactured from more or less parts including, but not limited to, two, three, five, six, etc. The various parts are preferably interconnected via interlocking projections 310g and recesses 310h, which may in turn be adhesively bonded, fastened or otherwise secured together to form the body 310. As generally shown, the core 380 may be manufactured from one part, although the core 380 may be manufactured from more parts including, but not limited to, two, three, four, etc.

Figure 15:
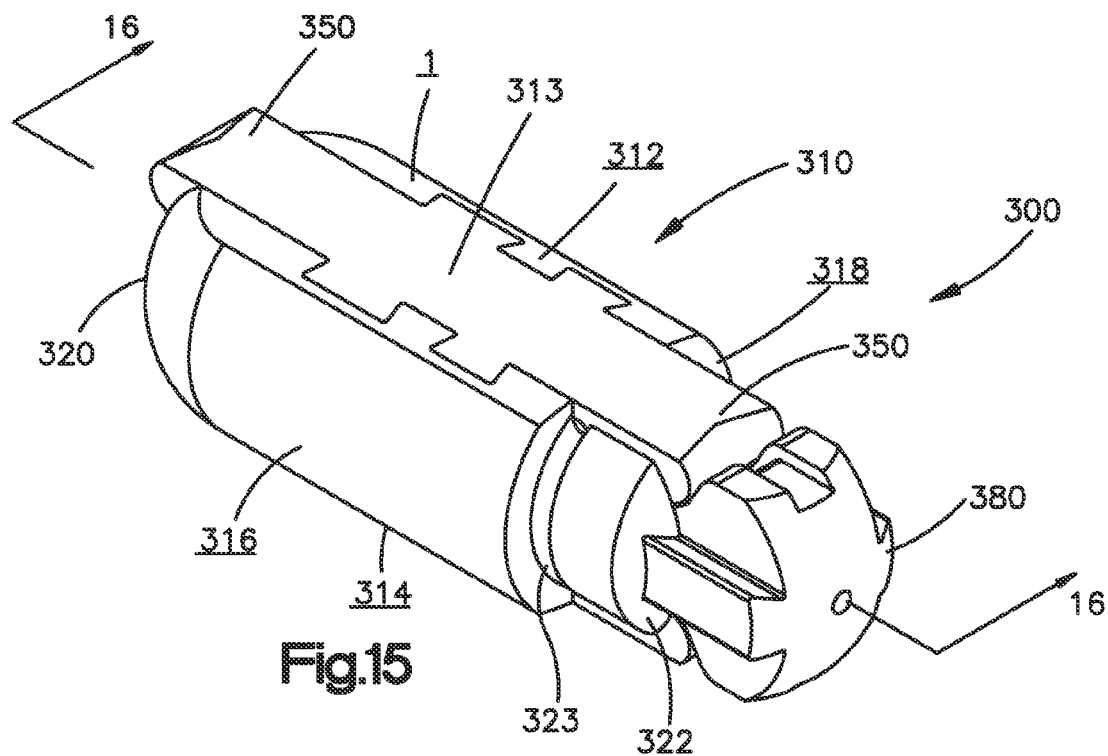
FIG. 15 is a side perspective view of a second preferred embodiment of an interspinous spacer according to the present invention, the spacer being shown in a first, insertion configuration.
Figure 16:
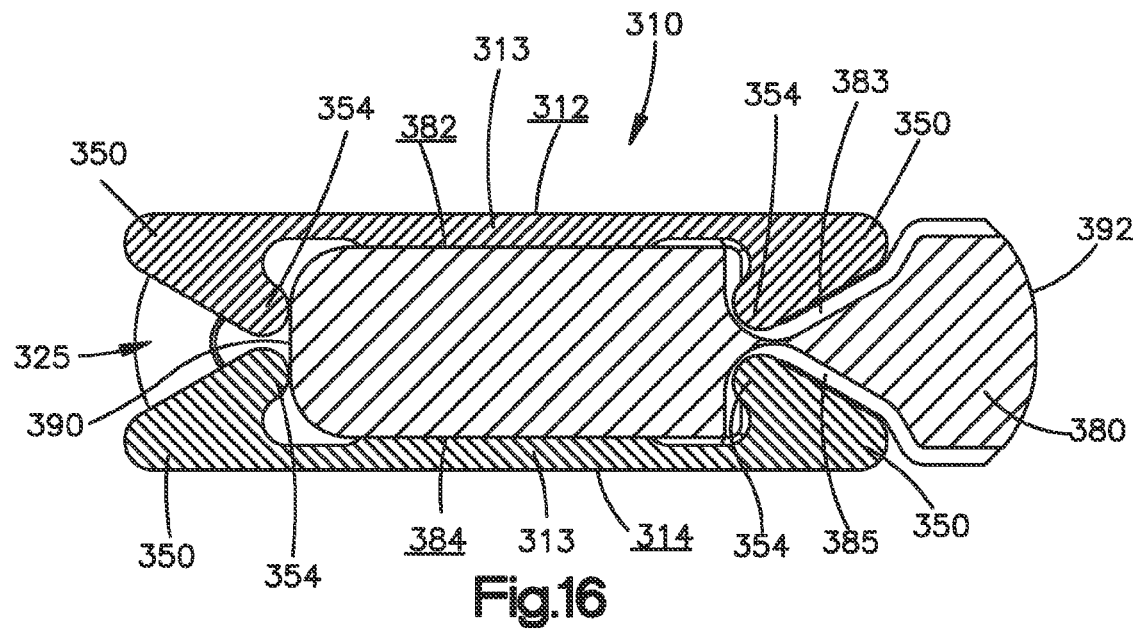
FIG. 16 is a cross-sectional view of the interspinous spacer shown in FIG. 15, taken along line 16-16 in FIG. 15.

Referring to FIGS. 15-19, the body 310 preferably includes deployable retainers 350 extending from a central portion 313 to assist in securing the spacer 300 between the adjacent spinous processes Sp. The interspinous spacer 300, including the body 310 and the retainers 350, may be demineralized to some level, as it is believed that the demineralizing process helps promote fusion between the spacer 300 and the adjacent spinous processes SP. However, it is envisioned that only the hinges 352 between the central portion 313 and the retainers 350 will undergo sufficient demineralization to render them flexible or to form living hinges at the hinges 352. Alternatively, it is envisioned that only the hinges 352 or the entire top and bottom bone contacting surfaces 312, 314 of the body 310 may be demineralized and thus flexible based on the demineralization process parameters (time of demineralization, acid concentration, use of masks, etc.). By sufficiently demeralizing the hinges 352 to render them flexible, the leading and trailing ends of the top and bottom bone contacting surfaces 312, 314 become moveable and/or pivotable relative to the central portion 313. In this manner, the deployable retainers 350 are integrally formed with the top and bottom bone contacting surfaces 312, 314 such that the body 310 may be inserted into the interspinous space with the retainers 350 in a first, insertion position (as generally shown in FIGS. 15 and 16). Once the body 350 has been positioned in the interspinous space, the retainers 350 are deployable to the second, deployed position (as generally shown in FIGS. 17 and 18) to prevent migration of the spacer 300 (i.e., to limit movement of the interspinous spacer 300 relative to the patient's spinous processes Sp). In the deployed position, the retainers 350 preferably extend from the top and bottom bone contacting surfaces 312, 314 and are located on either side of the spinous processes Sp between which the interspinous spacer 300 is positioned.

The second preferred embodiment of the interspinous spacer 300 is preferably designed and configured so that the body 310 and the core 380 can be preassembled at the time of manufacture, thereby preventing the surgeon from having to insert the core 380 into the bore 325 formed in the body 310 in situ (i.e., after the body has been inserted between the spinous processes Sp of adjacent vertebrae V). This may be accomplished by incorporating a pair of recesses 383, 385 in the core 380. The recesses 383, 385 preferably extend from the top and bottom surfaces 382, 384, respectively, adjacent the trailing end 392 so that the core 380 can be inserted into the bore 325 formed in the body 310 by the manufacturer with the retainers 350 in the first, insertion position. In addition, the leading end 390 of the core 380 is preferably sized and configured so as to not contact the projections 354 extending from the retainers 350 adjacent the leading end 320 of the body 310 when the core 380 is initially positioned in the bore 325 for shipping. Alternatively, the core 380 may include an additional pair of recesses (not shown) for aligning with the projections 354 adjacent to the leading end 320 of the body 310. In this manner, the core 380 can be received within the body 310, with the core 380 in a first position, and the body 310 can remain in the first, insertion configuration.

Alternatively, the body 310 and core 380 may take on other configurations that would permit the core 310 and body 380 to be preassembled. For example, referring to FIG. 42, the core 380' may include a first core portion 380a' for contacting the projections 354 formed on the retainers 350 adjacent to the leading end 320 and a second core portion 380b' for contacting the projections 354 formed on the retainers 350 adjacent the trailing end 322. The first and second core portions 380a', 380b' are preferably sized and configured to be coupled to the body 310 in the first, insertion configuration with the body 310 remaining in the first, insertion configuration. The first and second core portions 380a', 380b' may be coupled to one another via an intermediate core portion 380c'.

In use, the retainers 350 are deployed by moving the core 380 from the first position wherein the retainers 350 adjacent the trailing end 322 of the body 310 are aligned with the recesses 383, 385 formed in the core 380 (as generally shown in FIGS. 15 and 16) to the second, deployed position wherein the core 380 contacts the projections 354 to deploy the retainers 350 (as generally shown in FIGS. 17 and 18). That is, as best shown in FIG. 16, each of the deployable retainers 350 includes a projection 354 protruding into the bore 325 of the body 310, in the first, insertion configuration, the projections 354 formed on the retainers 350 adjacent the trailing end 322 are aligned with the recesses 383, 385 formed in the core 380. Thereafter, distal movement of the core 380 from its first position to its second position causes the core 380 to contact the projections 354, which in turn causes the retainers 350 to move from their first, insertion configuration to their second, deployed configuration.

In addition, the core 380 may include a core locking mechanism (not shown) for securing the final position of the core 380 with respect to the body 310, as previously described in connection with interspinous spacer 100.

Referring to FIGS. 15, 20-26 and 38, the body 310 preferably includes the engagement feature 323 for coupling to an insertion instrument 400. The engagement feature 323 can be any feature and/or element now or hereafter known for such purpose. Preferably, the engagement feature 323 is comprised of a groove extending circumferential around the first and second side surfaces 316, 318 adjacent to the trailing end 322 for engaging a plurality of fingers 415 extending from the insertion instrument 400. More specifically, the insertion instrument 400 preferably includes an outer cannulated shaft 410. The shaft 410 may have any shape known in the art. However the shaft 410 preferably has an oblong shape for matching the oblong shape of the interspinous spacer 300 and to facilitate the orientation and insertion of the spacer 300 relative to an insertion sleeve 1200, as will be described in greater detail below. The shaft 410 includes a distal end 412 and a proximal end 414. The distal end 412 of the shaft 410 includes a pair of flexible arms 415 for interlocking with the engagement feature 323 (i.e., groove) formed at the trailing end 322 of the body 310 to securely hold the spacer 300.

In addition, the distal end 412 of the shaft 410 includes a plunger 425 and a pair of dowel pins 430. Preferably, the plunger 425 is designed to be threaded, however it is envisioned that the plunger 425 may be slidably disposed within the shaft 410. The plunger 425 preferably includes a threaded portion 426 located on a proximal end thereof, an intermediate tapered section 427, and a distal pushing surface 428. In use, the plunger 425 moves (i.e., pushes) the core 380 from its first position (as shown in FIGS. 15 and 16) to its second position (as shown in FIGS. 17 and 18), thereby deploying the retainers 350. In addition, the plunger 425 releases the body 310 from the insertion instrument 400 so that the instrument 400 can be removed from the surgical site, leaving the spacer 300 behind in place.

Referring to FIGS. 24-26, by incorporating a threaded plunger 425, rotation of the plunger 425 in a clockwise direction advances the plunger 425 distally from its initial position (as generally shown in FIG. 24) toward the spacer 300, eventually causing the plunger 425 to contact the trailing end 392 of the core 380 (as generally shown in FIG. 25). As the plunger 425 is advanced further, the core 380 is pushed into its second position, deploying the retainers 350 (as is generally shown in FIG. 26). At the same time that the core 350 is pushed into its second position, the tapered section 427 contacts the dowel pins 430 such that further advancement of the plunger 425 pushes the dowel pins 427 outward in a radial direction causing the flexible arms 415 to spread apart, releasing the spacer 300.

Figure 23:
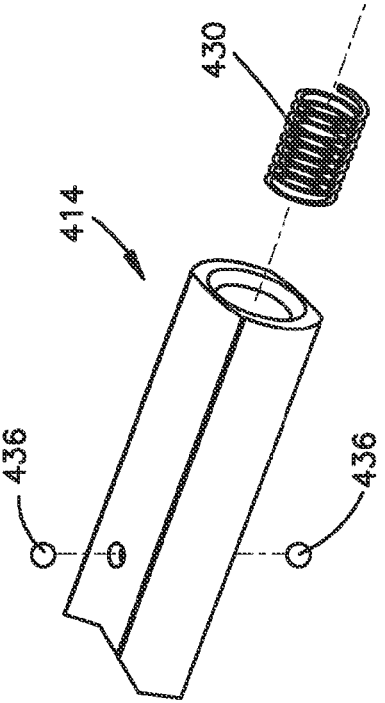
FIG. 23 is an exploded view of a proximal end of the insertion instrument shown in FIG. 20.

Referring to FIG. 23, the proximal end 414 of the insertion instrument 400 preferably includes a spring 430, a second plunger 432, a cap 434 and a plurality of ball bearings 436. The spring 430 and the second plunger 432 are designed such that when the second plunger 432 is in its free state, the ball bearings 436 are pushed outward in opposing radial directions from a longitudinal axis of the instrument 400 causing them to protrude beyond an outer surface of the shaft 410. However, as the second plunger 432 is pushed distally, the spring 430 is compressed and the ball bearings 436 are allowed to fall into a groove 433 formed in the second plunger 432. The cap 434 provides a gripping surface for the surgeon. The size and shape of the cap 434 could be modified to create a surface that is more "handle-like" than what is shown in the figures. The cap 434 also serves to hold the components in place. This creates a retention mechanism that allows the insertion instrument 400 to be mechanically coupled to an appropriate insertion sleeve 1200, locking the position of the spacer 300 and allowing the insertion sleeve 1200 and insertion instrument 400 to be removed from the surgical site as a single unit. Alternatively, the insertion instrument 400 may include any other retention mechanism now or hereafter known for coupling the insertion instrument 400 to the insertion sleeve 1200 including, for example, a threaded nut having clamping arms for engaging the sleeve 1200, projections extending from a cap for engaging the sleeve 1200, etc.

Referring to FIGS. 27-29, a third preferred embodiment of the interspinous spacer 500 includes a body member 510 and a core 580. The body member 510 is preferably, operatively associated with a plurality of deployable retainers 550 and has a bore 525 for receiving the core 580. The interspinous spacer 500 of the third preferred embodiment is similar to interspinous spacer 300 of the second preferred embodiment described above, as such the same reference numerals will be utilized to describe similar or the same components and the description will focus on the specific features of interspinous spacer 500 that distinguish it from interspinous spacer 300.

The body 510 is preferably sized and configured for positioning in the interspinous space between spinous processes Sp of adjacent vertebrae V. The body 510 includes a top bone contacting surface 512, a bottom bone contacting surface 514, a first side surface 516, a second side surface 518, a leading end 520 and a trailing end 522. The body 510 may be any shape, for example, round, polygonal, etc. Preferably the body 510 has an oblong shape. The trailing end 522 preferably includes one or more engagement features (such as engagement feature or groove 323 discussed above) for mating with an insertion instrument (such as insertion instrument 400 discussed above) for inserting the spacer 500 between the adjacent spinous processes Sp. The body 510 further includes the bore 525 extending from the trailing end 522. The bore 525 may extend partially or completely through the body 510 to the leading end 520. The body 510 preferably includes deployable retainers 550 to assist in securing the spacer 500 between the adjacent spinous processes Sp.

The core 580 is preferably sized and configured for insertion into the bore 525 formed in the body 510. The core 580 includes a top surface 582, a bottom surface 584, a first side surface 586, a second side surface 588, a leading end 590 and a trailing end 592. The core 580 may be any shape, for example, round, polygonal, etc. Preferably the core 580 has an oblong shape.

The body 510 and/or core 580 may be machined from a single piece of bone or may be machined from a plurality of bone pieces that are connected to one another via an attachment mechanisms, such as, for example, dovetails, pins, opposing taper locks, allograft welding, etc. and the bone pieces may further be bonded or fastened together to form the body 510 and/or the core 580. Referring to FIG. 29, for example, it is envisioned that the body 510 may be manufactured from a total of eight parts including a top bone contacting part 510a, a first top retainer 510b, a second top retainer 510c, a bottom bone contacting part 510d, a third bottom retainer 510e, a fourth bottom retainer 510f, a left side 510g and a right side 510h, although the body 510 may be manufactured from more or less parts. As will be described in greater detail below, the top and bottom bone contacting parts 510a, 510d may be interconnected to the first, second, third and fourth retainers 510b, 510c, 510e, 510f via bone pins 510x. The various remaining parts are preferably interconnected via interlocking projections and recesses. The core 580 may be constructed from one part, although the core 580 may be manufactured from more parts. In one exemplary embodiment, the interspinous spacer 500 of the third preferred embodiment may be demineralized to some level, as it is believed that the demineralizing process helps promote fusion between the spacer 500 and the adjacent spinous processes SP.

The third preferred embodiment of the interspinous spacer 500 is preferably designed and configured so that the deployable retainers 550 are coupled to the body 510 via bone pins 510x so that the retainers 550 are hingeably coupled to the body 510, thereby enabling them to pivot. In this manner, the spacer 500 may be inserted into the interspinous space between spinous processes Sp of adjacent vertebrae V with the retainers 550 in a first, insertion position (as generally shown in FIG. 27). Once positioned in the interspinous space, the retainers 550 are deployable to a second, deployed position (as generally shown in FIG. 28) to prevent migration of the spacer 500 (i.e., to limit movement of the interspinous spacer 500 relative to the patient's spinous processes Sp). In the deployed position, the retainers 550 preferably extend from the top and bottom bone contacting surfaces 512, 514 and are located on either side of the spinous processes Sp between which the interspinous spacer 500 is positioned. It should be noted, that the retainers 550 may also be "undeployed" by the surgeon for repositioning or removal of the spacer 500. In other words, the retainers 550 are movable from the second, deployed position to the first, insertion configuration so that the spacer 500 can be repositioned or removed from the interspinous space. The retainers 150, 350, 550, 650, 750 of each of the embodiments may be "undeployed" in a similar manner.

Similar to interspinous spacer 300 of the second preferred embodiment, the interspinous spacer 500 of the third preferred embodiment is designed and configured so that the body 510 and the core 580 can be preassembled at the time of manufacture, thereby preventing the surgeon from having to insert the core 580 into the bore 525 formed in the body 510 in situ (i.e., after the body 510 has been inserted between the spinous processes Sp of adjacent vertebrae V).

Figure 32:
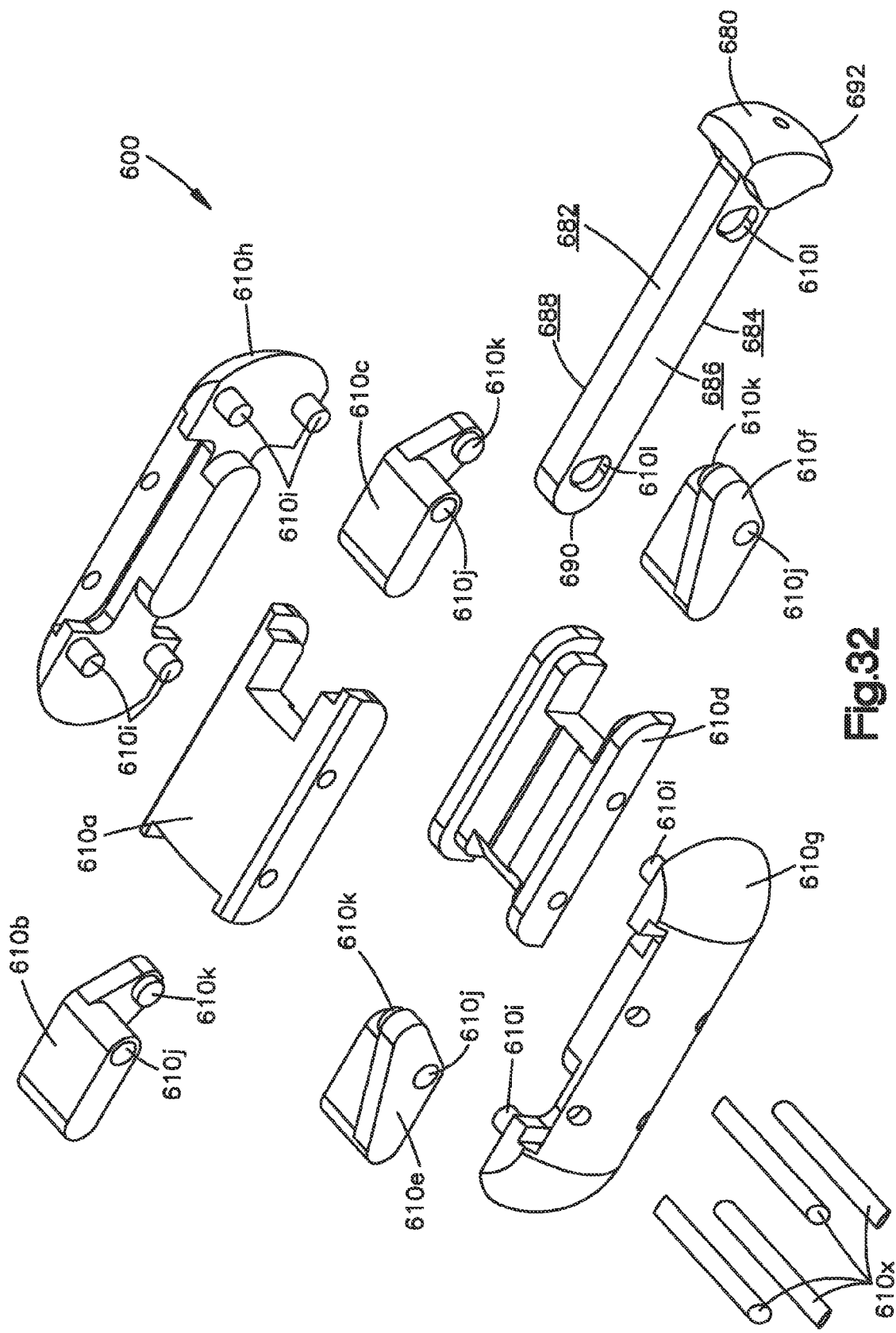
FIG. 32 is an exploded view of the spacer shown in FIG. 30.

Referring to FIGS. 30-32, a fourth preferred embodiment of the interspinous spacer 600 includes a body member 610 and a core 680. The body member 610 is operatively associated with a plurality of deployable retainers 650 and has a bore 625 for receiving the core 680. The interspinous spacer 600 of the fourth preferred embodiment is similar to the interspinous spacers 300, 500 of the second and third preferred embodiments, as such similar reference numerals will be utilized to describe similar or the same components and the description will focus on the specific features of interspinous spacer 600 of the fourth preferred embodiment that distinguish it from interspinous spacers 300, 500 of the second and third preferred embodiments.

The body 610 of the fourth preferred embodiment is sized and configured for positioning in the interspinous space between spinous processes Sp of adjacent vertebrae V. The body 610 includes a top bone contacting surface 612, a bottom bone contacting surface 614, a first side surface 616, a second side surface 618, a leading end 620 and a trailing end 622. The body 610 may be any shape, for example, round, polygonal, etc. Preferably the body 610 has an oblong shape. The trailing end 622 preferably includes one or more engagement features (such as the engagement feature or groove 323 of the second preferred embodiment discussed above) for mating with an insertion instrument (such as the insertion instrument 400 of the second preferred embodiment discussed above) for inserting the spacer 600 between the adjacent spinous processes Sp. The body 610 further includes a bore 625 extending from the trailing end 622. The bore 625 may extend partially or completely through the body 610 to the leading end 620.

The body 610 preferably includes deployable retainers 650 to assist in securing the spacer 600 between the adjacent spinous processes Sp.

The core 680 is sized and configured for insertion into the bore 625 formed in the body 610. The core 680 includes a top surface 682, a bottom surface 684, a first side surface 686, a second side surface 688, a leading end 690 and a trailing end 692. The core 680 may be any shape, for example, round, polygonal, rectangular, etc.

The body 610 and/or core 680 may be machined from a single piece of bone or may be machined from a plurality of bone pieces that are connected to one another via an attachment mechanisms, such as, for example, dovetails, pins, opposing taper locks, allograft welding, etc. Referring to FIG. 32, for example, it is envisioned that the body 610 may be manufactured from a total of eight parts including a top bone contacting part 610a, a first top retainer 610b, a second top retainer 610c, a bottom bone contacting part 610d, a third bottom retainer 610e, a fourth bottom retainer 610f, a left side 610g and a right side 610h, although the body 610 may be manufactured from more or less parts. As will be described in greater detail below, the left and rights sides 610g, 610h may be connected to the top and bottom bone contacting parts 610a, 610d via bone pins 610x. The left and rights sides 610g, 610h may be connected to the first, second, third and fourth retainers 610b, 610c, 610e, 610f by interconnecting projections 610i and holes 610j. In addition, the first, second, third and fourth retainers 610b, 610c, 610e, 610f may be interconnected to the core by interconnecting projections 610k and holes 610l.

The core 680 may be manufactured from one part, although the core 680 may be manufactured from more parts. In one exemplary embodiment, the interspinous spacer 600 may be demineralized to some level, as it is believed that the demineralizing process helps promote fusion between the spacer 600 and the adjacent spinous processes SP.

The fourth preferred embodiment of the interspinous spacer 600 is preferably designed and configured so that the deployable retainers 650 are coupled to the body 610 and to the core 680 via interconnecting projections and recesses 610i, 610j and 610k, 610l, respectively, so that the retainers 650 are hingeably coupled to the body 610 and the core 680, thereby enabling the retainers 650 to pivot in one direction as compared to the dual pivot direction of interspinous spacer 500 of the third preferred embodiment or as compared to demineralizing the hinges 352 of interspinous spacer 300 of the second preferred embodiment. By enabling the retainers 650 to pivot in one direction facilitates removal of the spacer 600, if necessary, from the interspinous space through the insertion sleeve 1200, as will be described in greater detail below, since the action of pulling the spacer 600 out through the sleeve 1200 will have the effect of pushing the retainers 650 back down into the first, insertion position. Thus, the retainers 650 may be "undeployed" by the surgeon for repositioning or removal of the spacer 600, if necessary. In other words, the retainers 650 are movable from the second, deployed position to the first, insertion configuration so that the spacer 600 can be repositioned or removed from the interspinous space.

The spacer 600 may be inserted into the interspinous space between spinous processes Sp of adjacent vertebrae V with the retainers 650 in a first, insertion position (as generally shown in FIG. 30). Once positioned in the interspinous space, the retainers 650 are deployable to a second, deployed position (as generally shown in FIG. 31) to prevent migration of the spacer 600 (i.e., to limit movement of the interspinous spacer 600 relative to the patient's spinous processes Sp). In the deployed position, the retainers 650 preferably extend from the top and bottom bone contacting surfaces 612, 614 and are located on either side of the spinous processes Sp between which the interspinous spacer 600 is positioned.

Similar to interspinous spacers 300, 500 of the second and third preferred embodiments, the interspinous spacer 600 is preferably designed and configured so that the body 610 and the core 680 can be preassembled at the time of manufacture, thereby preventing the surgeon from having to insert the core 680 into the bore 625 formed in the body 610 in situ (i.e., after the body 610 has been inserted between the spinous processes Sp of adjacent vertebrae V).

Referring to FIGS. 33 and 34, a fifth preferred embodiment of the interspinous spacer 700 includes a body member 710 and first and second core members 780a, 780b. In this fifth preferred embodiment, the first and second core members 780a, 780b are integrally formed with and/or include first and second pairs of deployable retainers 750a, 750b, respectively. The body member 710 includes a bore 725 for receiving the first and second core members 780a, 780b. The interspinous spacer 700 of the fifth preferred embodiment is similar to the interspinous spacer 100 of the first preferred embodiment and as such similar reference numerals will be utilized to describe similar or the same components and the description will focus on the specific features of interspinous spacer 700 of the fifth preferred embodiment that distinguish it from interspinous spacer 100 of the first preferred embodiment.

The body 710 of the fifth preferred embodiment is sized and configured for positioning in the interspinous space between spinous processes Sp of adjacent vertebrae V. The body 710 includes a top bone contacting surface 712, a bottom bone contacting surface 714, a first side surface 716, a second side surface 718, a leading end 720 and a trailing end 722. The body 710 may be any shape, for example, round, polygonal, etc. Preferably the body 710 has an oblong shape. The trailing end 722 preferably includes one or more engagement features (such as engagement feature or groove 123 discussed above) for mating with an insertion instrument (such as insertion instrument 200 discussed above) for inserting the body member 710 between the adjacent spinous processes Sp, as discussed above. The body 710 further includes a bore 725 extending from the trailing end 722. The bore 725 may extend partially or completely through the body 710 to the leading end 720.

The first and second core members 780a, 780b are sized and configured for sequential insertion into the bore 725 formed in the body 710. The first and second core members 780a, 780b include the first and second pair of deployable retainers 750a, 750b, respectively. The first and second pair of deployable retainers 750a, 750b are preferably attached to the first and second core members 780a, 780b by any mechanism now or hereafter known, such as, for example, via pins, hinges, demineralized hinges, etc., to allow the first and second pair of deployable retainers 750a, 750b to deploy when inserted into the bore 725 of the body 710. In use, the body 710 is inserted in a similar fashion as described above in connection with interspinous spacer 100 of the first preferred embodiment. That is, once the body 710 is positioned, the first and second core members 780a, 780b are sequentially inserted, which in turn causes the first pair of retainers 750a formed on the first core member 780a and the second pair of retainers 750b formed on the second core member 780b to deploy thru (i.e., radially out) the body member 710 on either side of the adjacent spinous processes Sp.

The body member 710 may include a first ramped surface (not shown) for contacting and deploying the first pair of deployable retainers 750a of the first core member 780a. The first core member 780a may also include a ramp surface 781 for contacting and deploying the second pair of deployable retainers 750b of the second core member 780b so that, in use, after the body member 710 is positioned in the interspinous space between adjacent spinous processes Sp, the surgeon may insert the first core member 780a into the bore 725 and then insert the second core member 780b. Insertion of the second core member 780b pushes the first core member 780a into contact with the ramped surface formed in the body member 710, which in turn, causes the first pair of deployable retainers 750a to deploy adjacent a first side of the spinous processes Sp. In addition, insertion of the second core member 780b, causes the second pair of deployable retainers 750b to contact the ramp surface 781 formed on the first core member 780a, which in turn, causes the second pair of deployable retainers 750b to deploy adjacent a second side of the spinous processes Sp. Alternatively, the surgeon may push the first core member 780a into contact with the ramped surface formed in the body member 710, which in turn, causes the first pair of deployable retainers 750a to deploy adjacent a first side of the spinous processes Sp and then may insert the second core member 780b until the second core member 780b contacts the ramp surface 781 formed on the first core member 780a, which in turn, causes the second pair of deployable retainers 750b to deploy adjacent a second side of the spinous processes Sp.

The body 710 and/or the first and second core members 780a, 780b may be machined from a single piece of bone or may be machined from a plurality of bone pieces that are connected to one another via an attachment mechanism, such as, for example, dovetails, pins, opposing taper locks, allograft welding, etc. The interspinous spacer 700 may be demineralized to some level, as it is believed that the demineralizing process helps promote fusion between the spacer 700 and the adjacent spinous processes SP.

Referring to FIGS. 1A-3, 5-9, 15-19, 24-28, 30, 31, 33, 34 and 41, in the preferred embodiments, the bodies 110, 310, 510, 610, 710 include an external boundary surface 1 that is generally defined by the top and bottom bone contacting surfaces 112, 114, 312, 314, 512, 514, 612, 614, 712, 714 and the first and second side surfaces 116, 118, 316, 318, 516, 518, 616, 618, 716, 718. In the first, insertion position the retainers 150, 350, 550, 650, 750a, 750b are located generally within the external boundary surface 1 (FIGS. 2, 3, 5-9, 15, 24, 25, 27, 30, 34, 39 and 40). In contrast, in the second, deployed position, the retainers 150, 350, 550, 650, 750a, 750b extend from and beyond the external boundary surface 1 (FIGS. 1A, 1B, 17, 18, 28, 31, 33 and 41). Specifically, the retainers 150, 350, 550, 650, 750a, 750b are positioned within the external boundary surface 1 such that the interspinous spacers 100, 300, 500, 600, 700 may be implanted through the insertion sleeve 1200. Accordingly, the retainers 150, 350, 550, 650, 750a, 750b may extend beyond the boundaries of the leading end 120, 320, 520, 620, 720, and/or the trailing end 122, 322, 522, 622, 722 in the first, insertion position, but the retainers 150, 350, 550, 650, 750a, 750b preferably do not extend beyond or only slightly beyond the boundaries of the top and bottom bone contacting surfaces 112, 114, 312, 314, 512, 514, 612, 614, 712, 714 and the first and second side surfaces 116, 118, 316, 318, 516, 518, 616, 618, 716, 718 or the external boundary surface 1 in the first, insertion position. However, the retainers 150, 350, 550, 650, 750a, 750b preferably extend beyond the external boundary surface 1 in the second, deployed position to generally secure the preferred interspinous spacers 100, 300, 500, 600, 700 relative to the spinous processes Sp of the adjacent vertebrae V when implanted in the patient's body.

Referring to FIGS. 35-41, an exemplary procedure for implanting the interspinous spacers 100, 300, 500, 600, 700 of the first through fifth preferred embodiments into the interspinous space between spinous processes Sp of adjacent vertebrae V will now be described. Various instruments may be used for insertion and/or removal of the spacers 100, 300, 500, 600, 700 such as, for example, a guide wire 1000, dilators 1100, 1102, insertion sleeve 1200, etc. Additional information is disclosed in U.S. patent application Ser. No. 11/198, 393, filed on Aug. 5, 2005, entitled "Apparatus for Treating Spinal Stenosis," the contents of which are hereby incorporated by reference in their entirety. While the instruments described below may be used with the spacers 100, 300, 500, 600, 700, one of ordinary skill in the art will readily appreciate that any number of instruments may be used in place of those described herein.

Preferably, the interspinous spacer 100, 300, 500, 600, 700 is configured to be inserted through a minimally invasive lateral approach using an insertion sleeve 1200 to provide a passageway to the interspinous space. The body 110, 310, 510, 610, 710 is preferably initially inserted into the interspinous space. Once the body 110, 310, 510, 610, 710 is positioned, the core 180, 180', 380, 380', 580, 680, 780 is either inserted into the bore 125, 325, 525, 625, 725 formed in the body 110, 310, 510, 610, 710 or the core 180, 180', 380, 380', 580, 680, 780 is moved from its first position to its second position to cause deployment of the retainers 150, 350, 550, 650, 750.

In one exemplary procedure, a lateral approach may be used to insert instrumentation into the patient's body. In the lateral approach, instrumentation is inserted through the side of a patient (e.g., the percutaneous passageway may be oriented substantially perpendicular to the spinous processes Sp or may be aligned with an axis passing between the spinous processes Sp). A lateral approach generally allows for a shorter recovery time and patients may be dismissed from hospital within the same day of the surgery. In other procedures, a posterior-lateral approach may be used for inserting instrumentation into the body.

Figure 35:
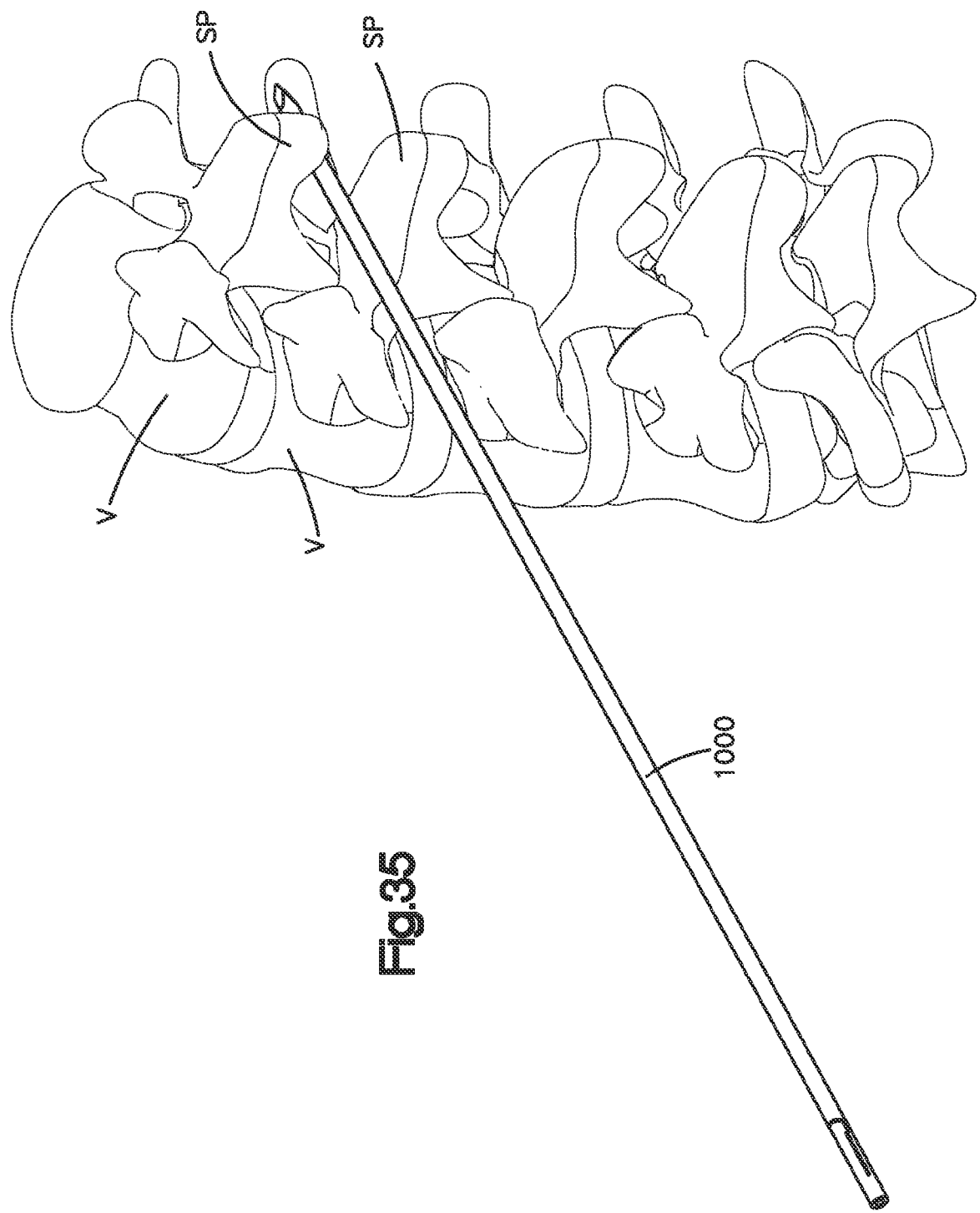

To perform a lateral procedure, the patient may be positioned in a manner to cause the desired amount of reduction of the lordosis (i.e., the interspinous space to open up) at the desired level. This may be achieved by placing the patient in a prone position with the patient's chest oriented horizontally (i.e., with the patient's chest lying on an operating table) and the patient's legs tilted towards the floor. The position of the spacer 100, 300, 500, 600, 700 in a lateral view can be predetermined by insertion of a guide wire 1000 through a small skin incision and into the interspinous space (as generally shown in FIG. 35). This step may be performed with the help of x-ray control. The tip of the guide wire 1000 may indicate the future position of the spacer 100, 300, 500, 600, 700. In some procedures, it may be necessary to use a longer guide wire. The guide wire 1000 may be extended by attaching an extension wire (not shown). The extension may enable a surgeon to hold the guide wire 1000 in place while one or more dilators 1100, 1102, insertion sleeve 1200 or other instruments are being introduced into the body.

Figure 36:
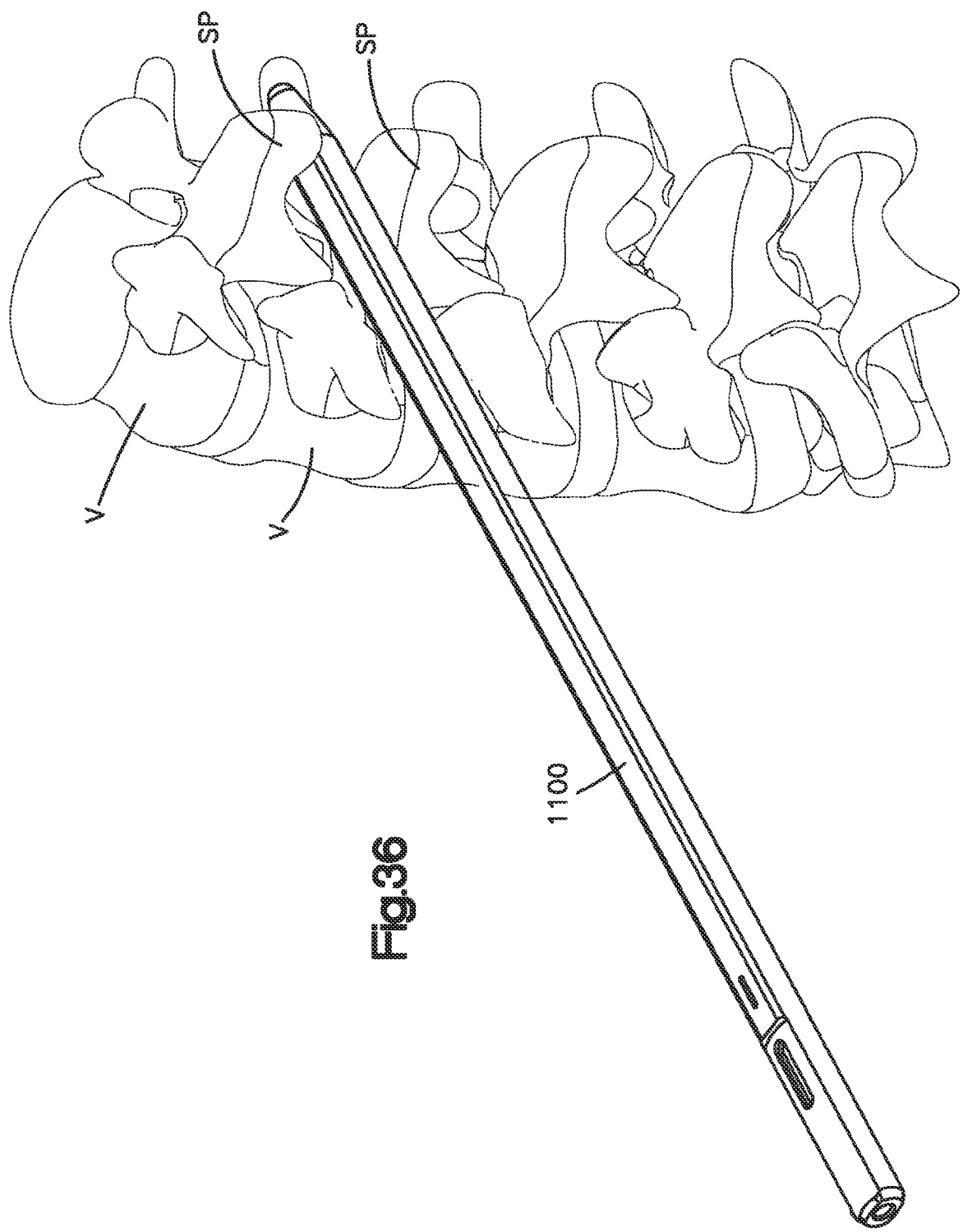
Figure 37:
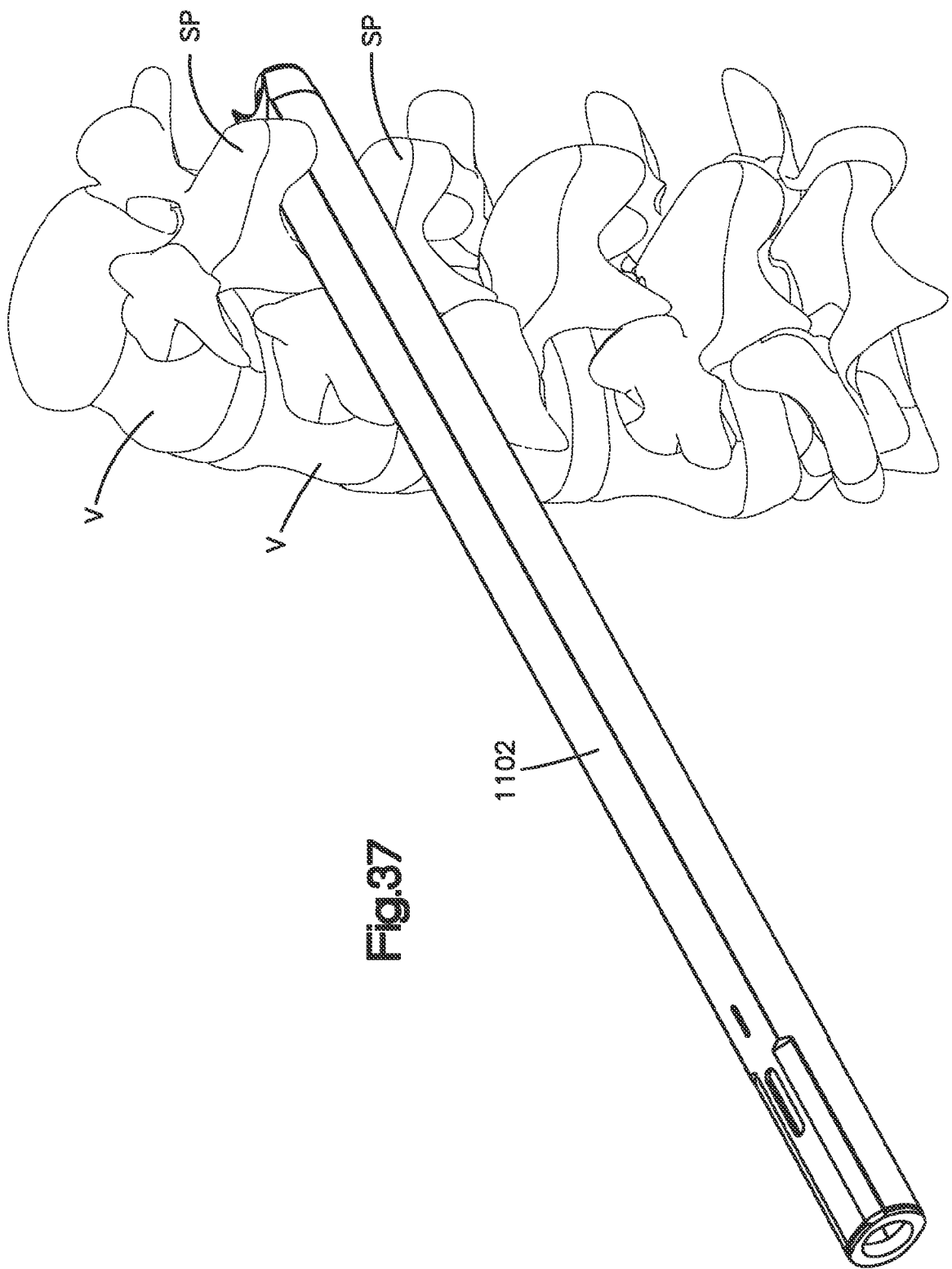
Figure 38:
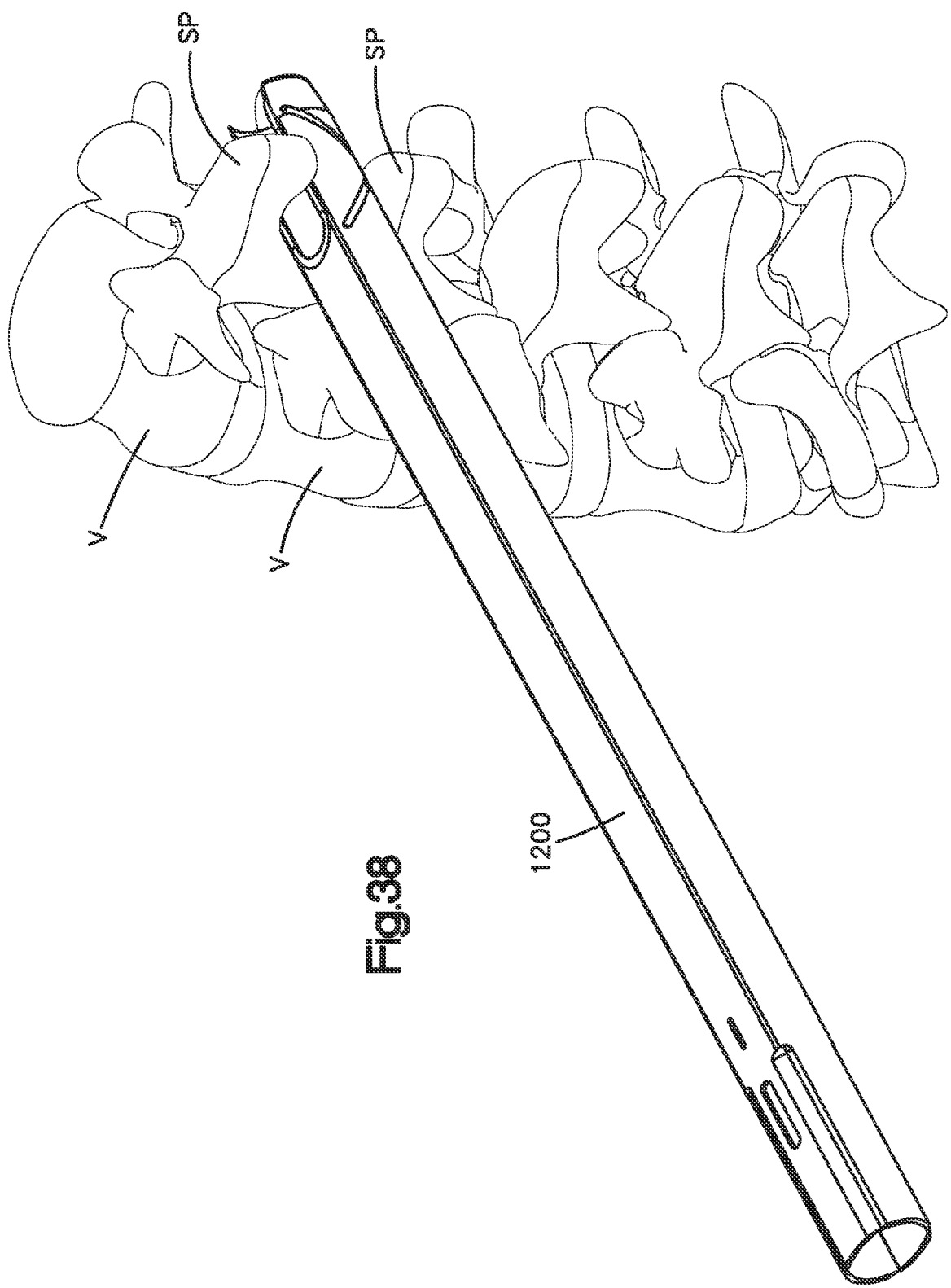

The passageway for the insertion of the spacer 100, 300, 500, 600, 700 may be prepared by stepwise dilation of soft tissues. Dilation may be achieved by introducing a first dilator 1100 over the guide wire 1000 (as generally shown in FIG. 36) followed by sequential insertion of additional dilators 1102 of increasing dimension/diameter (e.g., increments of 2 mm) (as generally shown in FIG. 37) until the outer diameter of the dilators 1102 touches or slightly distracts the spinous processes Sp. The outer diameter of the last dilator 1102 may be the same as the diameter of the interspinous spacer 100, 300, 500, 600, 700 which will be used. One or more insertion sleeve 1200 may be positioned over the last/largest dilator 1102 between the spinous processes Sp without causing any further distraction of the spinous processes Sp. The insertion sleeve 1200 creates the passageway for the spacer 100, 300, 500, 600, 700 to be inserted between the spinous processes Sp. With the outermost insertion sleeve 1200 in place, the guide wire 1000, dilator(s) 1100, 1102 and/or other insertion sleeve(s) may be removed from the body by, for example, pulling on the guide wire 1000 and/or extension wire. This may clear the inner diameter of the outermost insertion sleeve 1200 (as generally shown in FIG. 38).

Figure 39:
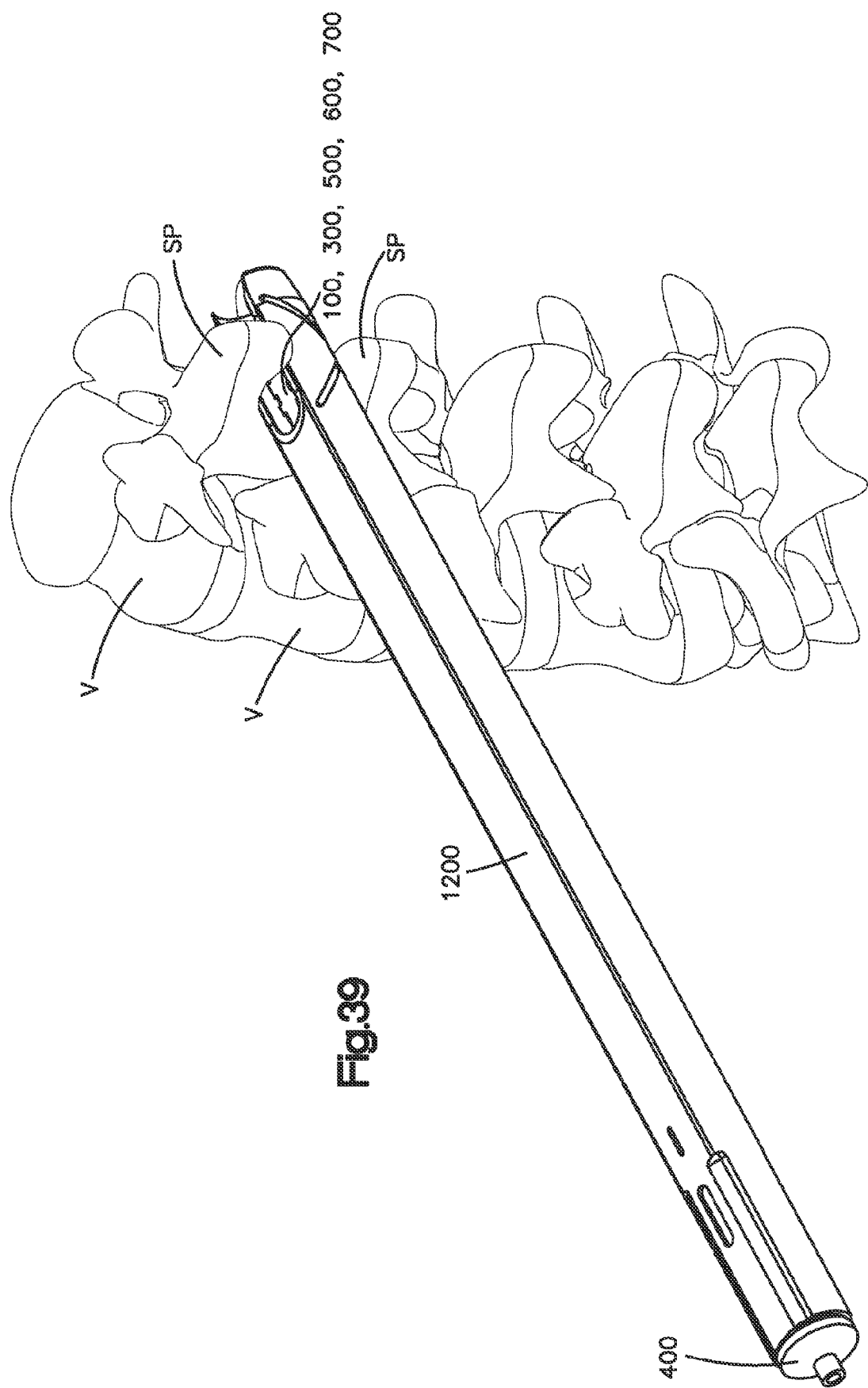
Figure 40:
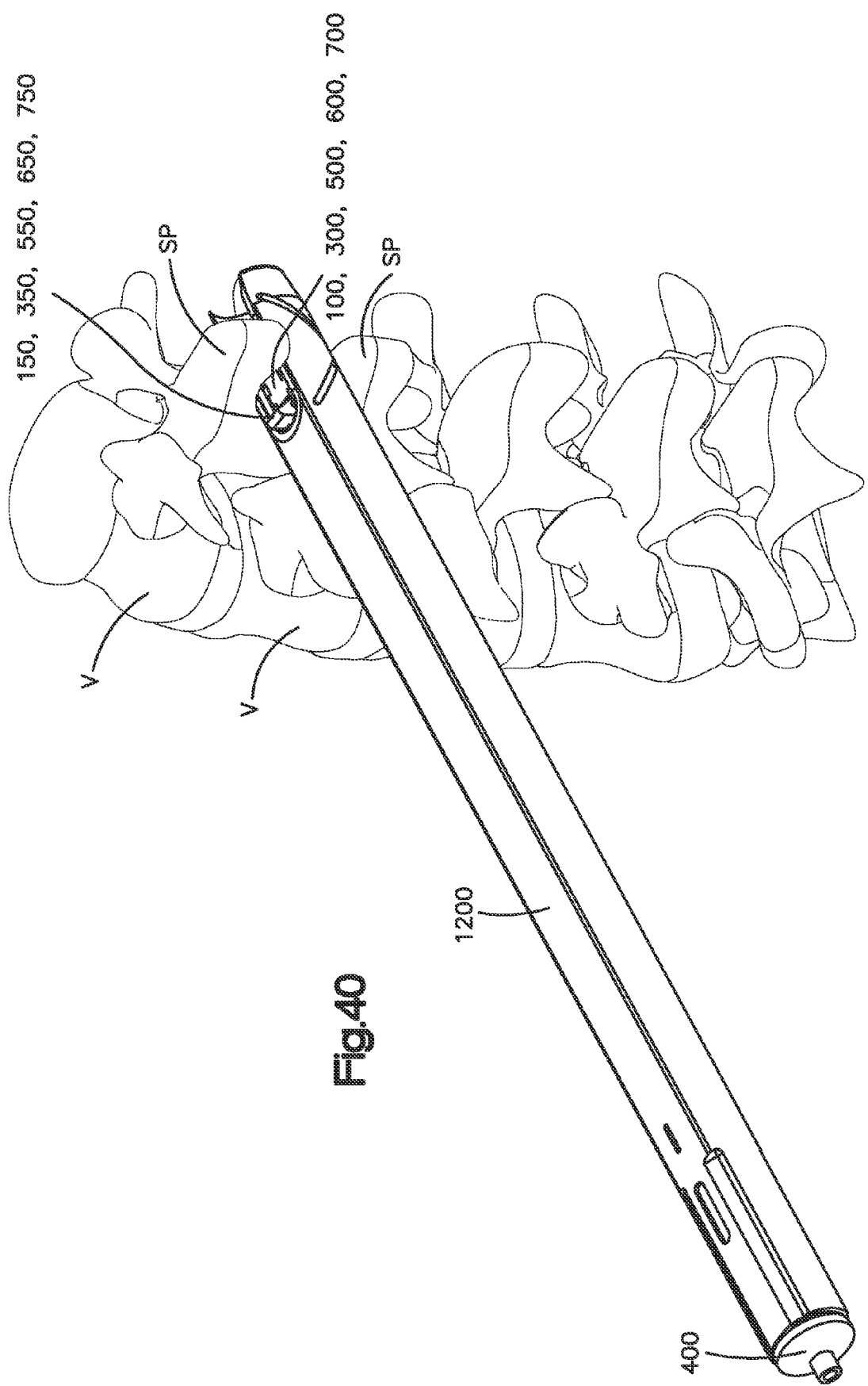

Thereafter, the interspinous spacer 100, 300, 500, 600, 700 may be inserted through the insertion sleeve 1200 using the insertion instrumentation 200, 250, 400 (shown as 400) as previously described (as generally shown in FIG. 39). The insertion instrumentation 200, 250, 400 may include stops which may ensure correct insertion depth and orientation of the spacer 100, 300, 500, 600, 700. Once the spacer 100, 300, 500, 600, 700 is positioned between the spinous processes Sp, the deployable retainers 150, 350, 550, 650, 750 formed on the spacer 100, 300, 500, 600, 700 may be deployed on both sides of the spinous processes Sp (as generally shown in FIG. 40). With the spacer 100, 300, 500, 600, 700 fully deployed, the insertion instrumentation 200, 250, 400 may be detached and removed from the patient's body with the insertion sleeve 1200, leaving the spacer 100, 300, 500, 600, 700 in place (as generally shown in FIG. 41). Finally, the incision may be sutured closed.

It should be understood that those of ordinary skill in the art will recognize many modifications and substitutions may be made to various elements of the present invention. For example, various features and/or elements have been described in connection with the preferred embodiments, which have not been described in another preferred embodiment. It is envisioned that these features and/or elements are interchangeable such that a feature or element described in one embodiment may be used in combination with another embodiment.

The interspinous spacers 100, 300, 500, 600, 700 of the preferred embodiments may be provided in a kit, which may include different sized body members, retainers and/or core members to enable the surgeon to account for differing patient's anatomies.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

We claim:

1. An interspinous spacer for insertion into an interspinous space between spinous processes of adjacent vertebrae, the spacer comprising:
a body including a top bone contacting surface, a bottom bone contacting surface, a first side surface, a second side surface, a leading end, a trailing end and a bore extending through the body from an opening in the trailing end in a direction towards an opening in the leading end, an external boundary surface of the body defined by the top and bottom bone contacting surfaces, the first and second side surfaces, the leading end and the trailing end;
a plurality of deployable retainers positioned at the top and bottom bone contacting surfaces of the body, each of the plurality of deployable retainers located at a position adjacent to a respective one of the leading end and the trailing end, each of the plurality of deployable retainers including a projection extending into the bore where a distance that the projection extends into the bore increases along the projection from the respective one of the leading and trailing ends towards a midline of the body; and
a core including a top surface, a bottom surface, a first side surface, a second side surface, a leading end and a trailing end, the core being movably receivable within the bore formed in the body and at least a portion of the core extends from the opening in the trailing end and the opening in the leading end when the core is received within the body, the body, plurality of deployable retainers and the core being constructed of bone,
wherein the body being sized and configured for implantation into the interspinous space with the plurality of retainers in a first, insertion configuration,
wherein the plurality of retainers are located generally within the external boundary surface, the retainers being urged to a second, deployed position by inserting the core into the bore and along the projections of the retainers such that at least a portion of the plurality of deployable retainers extends from the external boundary surface, in the second, deployed position, the retainers located adjacent the spinous processes.

2. The interspinous spacer of claim 1, wherein the body has an oblong shape.

3. The interspinous spacer of claim 1, wherein the trailing end of the body includes an engagement feature for mating with a body insertion instrument for inserting the body into the interspinous space.

4. The interspinous spacer of claim 3, wherein the engagement feature formed on the body is for engaging a plurality of fingers extending from the body insertion instrument.

5. The interspinous spacer of claim 1, wherein the trailing end of the core includes an engagement feature for mating with a core insertion instrument for inserting the core into the bore formed in the body.

6. The interspinous spacer of claim 5, wherein the engagement feature formed on the core is a recess formed in the top and bottom surfaces of the core adjacent to the trailing end of the core for engaging a plurality of fingers extending from the core insertion instrument.

7. The interspinous spacer of claim 6, wherein the core insertion instrument and the core are sized and configured to be insertable thru a cannulated bore formed in the body insertion instrument so that, after implantation of the body into the interspinous space, the core can be inserted through the cannulated bore formed in the body insertion instrument and into the bore formed in the body thereby deploying the retainers from their first, insertion configuration to their second, deployed configuration.

8. The interspinous spacer of claim 1, wherein the plurality of deployable retainers secured to the body by a hinge.

9. The interspinous spacer of claim 8 wherein the hinges are formed by demineralizing at least a portion of the body, the hinges being comprised of living hinges.

10. The interspinous spacer of claim 8, wherein the body is demineralized.

11. The interspinous spacer of claim 1, wherein each of the plurality of deployable retainers is pivotably coupled to the body by a pin so that the retainers are pivotable with respect to the top and bottom bone contacting surfaces.

12. The interspinous spacer of claim 1, wherein the core includes a core locking mechanism for securing a final position of the core with respect to the body.

13. The interspinous spacer of claim 12, wherein the core locking mechanism is a recess formed in the core for receiving a projection formed on one of the plurality of deployable retainers.

14. An interspinous spacer for insertion into an interspinous space between spinous processes of adjacent vertebrae, the spacer comprising:
a body including a top bone contacting surface, a bottom bone contacting surface, a first side surface, a second side surface, a leading end, a trailing end and a bore extending through the body from an opening in the trailing end in a direction towards an opening in the leading end;
a plurality of deployable retainers operatively associated with the top and bottom bone contacting surfaces of the body, each of the plurality of deployable retainers located at a position adjacent to a respective one of the leading end and the trailing end, each of the plurality of deployable retainers including a projection extending into the bore where a distance that the projection extends into the bore increases along the projection from the respective one of the leading and trailing ends towards a midline of the body; and
a core including a top surface, a bottom surface, a first side surface, a second side surface, a leading end and a trailing end, the core being slidably receivable within the bore formed in the body and at least a portion of the core extends from the opening in the trailing end and the opening in the leading end when the core is received within the body, the body, plurality of deployable retainers and the core being constructed of bone, the core being moveable between a first position and a second position,
wherein in the first position the plurality of retainers are in a first, insertion configuration and in the second position, the plurality of retainers are in a second, deployed configuration,
wherein the body is sized and configured for implantation into the interspinous space with the core in the first position and the plurality of retainers in the first, insertion configuration and after the body has been implanted into the interspinous space, the core is moved along the projection of the retainers to the second position causing the plurality of deployable retainers to deploy to the second, deployed configuration such that the plurality of deployable retainers extend from the top and bottom bone contacting surfaces, respectively.

15. The interspinous spacer of claim 14, wherein the body has an oblong shape.

16. The interspinous spacer of claim 14, wherein the body includes hinges pivotably connecting the plurality of deployable retainers thereto, the hinges being constructed of demineralized portions proximate the top and bottom bone contacting surfaces.

17. The interspinous spacer of claim 14, wherein each of the plurality of deployable retainers is pivotably coupled to the spacer by a pin so that each of the plurality of retainers can pivot with respect to the top and bottom bone contacting surfaces.

18. The interspinous spacer of claim 14, wherein movement of the core from the first position to the second position causes the core to contact the projections causing the plurality of retainers to deploy to their second, deployed configuration.

19. The interspinous spacer of claim 18, wherein the core includes one or more recesses extending from the top and bottom surfaces of the core adjacent the trailing end so that in the first position the projections formed on the retainers align with the recesses formed in the core.

20. The interspinous spacer of claim 19, wherein the body includes an engagement feature for coupling to an insertion instrument.

21. The interspinous spacer of claim 14, wherein the core includes a core locking mechanism for securing a final position of the core with respect to the body.

22. The interspinous spacer of claim 21, wherein the core locking mechanism is a recess formed in the core for receiving one of the projections formed on the plurality of deployable retainers.

23. The interspinous spacer of claim 14, wherein the core and the body are interconnected by a locking interface.

24. The interspinous spacer of claim 14, wherein the body is demineralized to facilitate fusion between the spacer and the adjacent spinous processes.

25. A method for lateral insertion of an interspinous spacer into an interspinous space between superior and inferior interspinous processes, the spacer including a body operatively associated with a plurality of deployable retainers and a core, the method comprising the steps of:
accessing the interspinous space laterally;
inserting the body between the superior and inferior spinous processes and into the interspinous space with the plurality of retainers being located in a first, insertion position from a first lateral side of the spinous processes; and inserting the core into a bore extending through the body from an opening in a trailing end of the body towards an opening in the leading end of the body, where inserting the core causes the plurality of deployable retainers to move to a second, deployed configuration so that the retainers extend from a respective one of a first end and a second end of the body such that the retainers are positioned adjacent to first and second lateral sides of at least one of the upper and lower spinous processes, the deployable retainers including a projection extending into the bore where a distance that the projection extends into the bore increases along the projection from the respective one of the leading and trailing ends toward a midline of the body, the deployable retainers moving to the second, deployed configuration by moving the core along the projections thereby pivoting the deployable retainers about a hinge comprised of a living hinge, the living hinge constructed of demineralized bone, and at least a portion of the core extending from the opening in the trailing end and the opening in the leading end.

* * * * *